US006087140A

United States Patent [19]
Cameron et al.

[11] Patent Number: 6,087,140
[45] Date of Patent: *Jul. 11, 2000

[54] MICROBIAL PRODUCTION OF 1,2-PROPANEDIOL FROM SUGAR

[75] Inventors: Douglas C. Cameron; Anita J. Shaw; Nedim E. Altaras, all of Madison, Wis.

[73] Assignee: Wisconsin Alumni Research Foundation, Madison, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/801,344

[22] Filed: Feb. 19, 1997

[51] Int. Cl.⁷ ....................................................... C12P 7/18
[52] U.S. Cl. ........................... 435/158; 435/189; 435/183; 435/252.3; 435/252.33; 536/23.2; 536/23.1
[58] Field of Search ..................................... 435/158, 189, 435/252.33, 320.1, 173; 536/23.2, 23.1

[56] References Cited

U.S. PATENT DOCUMENTS 5,677,124  10/1997  DuBois et al. ................................ 435/5
5,686,276  11/1997  Laffend et al. ........................... 435/158

OTHER PUBLICATIONS

Percy et al. "Cloning, expression, and characterization of methyglyoxal synthase from *Escherichia coli*" American Society for Biochemistry and Molecular Biology Meeting Abstract, Protein Structure Section, No. 1367, Jun. 2–6, 1996.
Ackerman, R.S., Cozzarelli, R., Epstein, W. (1974) *J. Bact.* 119:357–362.
Cameron, D.C. and C.L. Cooney (1986) *Bio/Technology* 4:651–654.
Franklin Associates, Ltd. (1994) "Life Cycle Assessment of Ethylene Glycol and Propylene Glycol Based Antifreeze," Franklin Associates, Prairie Village, Kansas.
Freedberg, W.B., Kistler, W.S., Lin, E.C.C. (1971) *J.Bact.* 108:137–144.
Gait, A.J. "Propylene Oxide," In: E.G. Hancock (ed.), *Propylene and its Industrial Derivatives*, p. 273–297, John Wiley and Sons, NY, NY (1973).
Ghalambor, M.A.; Heath, E.C. (1962) *J. Biol. Chem.* 237:2427–2433.
Hill, J.E., Myers, A.M., Koerner, T.J., Tzagoloff, A. (1986) *Yeast* 2:163–167.
Hopper, D.J., and Cooper, R.A. (1972) *Biochem J.* 128:321–329.
Kadner, R.J., Murphy, G.P., Stephens, C.M. (1992) *J. Gen. Microbio.* 138:2007–2014.
Koob, M.D., Shaw, A.J., and Cameron, D.C. (1994) *Proc. N.Y. Acad. Sci.* 745:1–3.
Old, S.E., Sato, S., Kador, P.F., and Carper, D.A. (1990) *Proc. Natl. Acad. Sci.* 87:4942–4945.
Sambrook, Fritsch, and Maniatis (1986) "Molecular Cloning, A Laboratory Manual," 2nd Ed., Strategies for Cloning in Plasmid Vectors, 1.53–1.59 and Ligation Reactions, 1.63–1.73.
Sawada, H.; Takagi, Y. (1964) *Biochim. Biophys. Acta,* 92:26–32.
Simon, E.S., Whitesides, G.M., Cameron, D.C., Weitz, D.J., and Cooney, C.L. (1987) *J. Org. Chem.* 52:4042–4044.
Sridhara, S.; Wu, T.T. (1969) *J. Biol. Chem.* 244:5233–5238.
Tran–Din, K. and G. Gottschalk (1985) *Arch.Microbiol.* 142:87–92.
Jagt et al. "Reduction of trioses by NADPH–dependent aldo–keto reductases" J. Biol. Chem. 267, 4364–4369, Mar. 1992.
Clarke et al. "Nucleotide sequence of the pntA and pntB genes coding the pyridine nucleotide transhydrogenase of *Escherichia coli*" Eurp. J. Biochem. 158, 647–653, 1986.
Carper et al. Aldose reductase and p–crystalline belong to the same protein superfamily as aldehyde reductase 220, 209–213, Aug. 1987.
Conway et al. "{Similarity of *Escherichia coli* propanediol oxidoreductase (fucO Product) and unusual Dehydrogenase from *Zymomonas mobilis* and *Saccharomyces cerevisiae*" J. Bacteriol. 171, 3754–3759, Jul. 1989.

*Primary Examiner*—Nashaat Nashed
*Attorney, Agent, or Firm*—DeWitt Ross & Stevens S.C.

[57] ABSTRACT

Microorganisms which ferment common sugars into 1,2-propanediol, synthetic operons to effect the transformation, and methods to produce 1,2-propanediol by fermentation of common sugars using the transformed microorganisms are disclosed.

10 Claims, 7 Drawing Sheets

MICROBIAL PRODUCTION OF 1,2-PROPANEDIOL FROM SUGAR

This invention was made with United States government support awarded by the following agencies: Environmental Protection Agency, Grant No. 900713Z3; National Institutes of Health, Grant No. GM08349. The United States government has certain rights in this invention.

FIELD OF THE INVENTION

The invention is drawn to microorganisms and their use in the production of 1,2-propanediol via microbial fermentation of common sugars. More specifically, the present invention is drawn to recombinant microorganisms having reductive enzyme activity or activities which enable the recombinant microorganism to ferment common sugars to 1,2-propanediol.

BIBLIOGRAPHY

Complete bibliographic citations to the references mentioned below are included in the Bibliography section, immediately preceding the claims. Each of the references mentioned below is incorporated herein by reference in its entirety.

DESCRIPTION OF THE PRIOR ART 1,2-Propanediol (1,2-PD; also known as propylene glycol) is a major commodity chemical with an annual production greater than one billion pounds in the United States. The major utilization of 1,2-PD is in unsaturated polyester resins, liquid laundry detergents, pharmaceuticals, cosmetics, antifreeze and de-icing formulations.

1,2-PD is conventionally produced from petrochemicals. Unfortunately, several toxic chemicals, such as chlorine, propylene oxide, and propylene chlorohydrin are either required or are produced as by-products in the conventional synthesis. In the conventional route, 1,2-PD is produced by the hydration of propylene oxide, which is obtained from propylene. The synthetic process produces racemic 1,2-PD, an equimolar mixture of the two enantiomers. This chemical process has a number of disadvantages, including the use of large quantities of water to minimize the production of polyglycols. The major problem, however, with the conventional synthetic route to 1,2-PD arises in the production of its intermediate, propylene oxide.

Propylene oxide is manufactured by one of two standard commercial processes: the chlorohydrin process or the hydroperoxide process. The chlorohydrin process involves toxic chlorinated intermediates and the use of caustic or lime. Additionally, this process may result in air emissions of propylene chlorohydrin and chlorine. (Franklin Associates, Ltd. (1994).) The hydroperoxide process involves oxidation of propylene by an organic hydroperoxide and results in the stoichiometric co-production of either tertbutanol or 1-phenyl ethanol. This make the economics of the production of propylene oxide via the hydroperoxide route directly related to the market for the co-produced byproducts. (Gait (1973).)

It is known that 1,2-PD is produced by several organisms when grown on exotic sugars. As early as 1937, the fermentation of L-rhamnose to 1,2-PD (later shown to be the S enantiomer) was described by Kluyver and Schnellen (1937). In *E. coli* and a variety of other microorganisms, L-rhamnose and L-fucose are metabolized to L-lactaldehyde and dihydroxyacetone phosphate. (Sawada and Takagi (1964) and Ghalambor and Heath (1962), respectively.) Under aerobic conditions, L-lactaldehyde is oxidized in two steps to pyruvate (Sridhara and Wu (1969)). Under anaerobic conditions, however, L-lactaldehyde is reduced to S-1,2-PD by a nicotinamide adenine nucleotide (NAD)-linked 1,2-propanediol oxidoreductase (*EC* 1.1.1.77). The S-1,2-PD produced diffuses into the extra-cellular medium.

Although a variety of microorganisms, including *E. coli*, produce S-1,2-PD from 6-deoxyhexose sugars, Obradors et al. (1988), this route is not commercially feasible because these sugars are extremely expensive. The least expensive of these 6-deoxyhexose sugars, L-rhamnose, currently sells for approximately $325 per kilogram (Pfanstiehl Laboratories, Chicago, Ill.).

In the mid-1980's, organisms capable of fermenting common sugars, such as glucose and xylose, to R-1,2-PD were discovered. See, for instance, Tran-Din and Gottschalk (1985). *Clostridium sphenoides* produces R-1,2-PD via a methylglyoxal intermediate. In this pathway, dihydroxyacetone phosphate (DHAP) is converted to methylglyoxal (MG) by the action of methylglyoxal synthase. The MG is reduced stereospecifically to give D-lactaldehyde. The D-lactaldehyde is then further reduced to give R-1,2-PD. The commercial production of 1,2-PD by *C. sphenoides* is severely limited, however, by the fact it is only produced under phosphate limitation; it is both difficult and expensive to obtain commercial-grade medium components which are free of phosphate. Additionally, only low titers of 1,2-PD are achieved.

*Thermoanaerobacterium thermosaccharolyticum* HG-8 (formerly *Clostridium thermosaccharolyticum*, ATCC 31960) also produces R-1,2-PD via methylglyoxal. Cameron and Cooney (1986). As with *C. sphenoides*, DHAP is converted to MG. The MG is then reduced at the aldehyde group to yield acetol. The acetol is then further reduced at the ketone group to give R-1,2-PD. For both *C. sphenoides* and *T. thermosaccharolyticum* HG-8, the enzymes responsible for the production of 1,2-PD have not been identified or cloned.

SUMMARY OF THE INVENTION

The invention is directed to a method of producing 1,2-propanediol by fermentation of sugars. The method comprises culturing a microorganism which expresses one or more enzymes which catalyze production of 1,2-propanediol from intracellular methylglyoxal in a medium containing a sugar carbon source other than a 6-deoxyhexose sugar, whereby the sugar carbon source is metabolized into 1,2-propanediol. Preferably, the method utilizes a recombinant organism containing one or more recombinant genes whose encoded gene products catalyze the reduction of methylglyoxal to 1,2-propanediol.

More specifically, the invention is directed to a method of producing 1,2-propanediol by fermentation with recombinant *E. coli* or yeast which comprises culturing a recombinant *E. coli* or yeast in a medium containing a sugar carbon source selected from the group consisting of arabinose, fructose, galactose, glucose, lactose, maltose, sucrose, xylose, and combinations thereof. The recombinant *E. coli* or yeast includes one or more recombinant genes which encode enzymes selected from the group consisting of aldose reductase, glycerol dehydrogenase, or combinations thereof.

The invention is also drawn to a synthetic operon which enables the production of 1,2-propandiol in a microorganism transformed to contain the operon. The operon includes one or more genes whose encoded gene products catalyze the reduction of methylglyoxal to 1,2-PD and a promoter sequence operationally linked to the one or more genes.

In a preferred embodiment, the synthetic operon includes at least one promoter sequence, a gene selected from the group consisting of an aldose reductase gene, a glycerol dehydrogenase gene, and combinations thereof; and a gene selected from the group consisting of a methylglyoxal synthase gene, a pyridine nucleotide transferase gene, and combinations thereof, wherein the genes are operationally linked to the promoter.

The invention is also drawn to E. coli transformed to contain the synthetic operon.

In short, the present invention is drawn to the use of microorganisms, preferably recombinant E. coli or S. cerevisiae, which express reductive enzyme activity which enables them to produce 1,2-PD, presumably via a reductive pathway leading from methylglyoxal to acetol (or lactaldehyde) to 1,2-PD.

If a recombinant microorganism is utilized, the gene sequences encoding the reductive enzyme activity may reside on plasmids within the microorganism, or the gene sequences may be integrated into the chromosome. It is preferred that the recombinant gene sequences be integrated into the genome of the microorganism.

The invention utilizes microorganisms which express enzymes which enable the production of 1,2-PD from the fermentation of common sugars. As used herein, the term "common sugars" refers to readily available sugars including, but not limited to, arabinose, fructose, galactose, glucose, lactose, maltose, sucrose, and xylose. Specifically excluded from the term "common sugars" are 6-deoxyhexose sugars such as rhamnose and fucose.

While not being limited to a particular cellular mode of action, it is thought that by properly manipulating enzyme activity, intracellular MG is enzymatically reduced to yield 1,2-PD, which is then secreted into the extracellular environment.

The production of MG in the host microorganism can also be simultaneously increased, thereby increasing the production of 1,2-PD. Methylglyoxal production can be maximized by fermenting under phosphate limitation or with the addition of cAMP, as well as by several other methods known to the art. Additionally, selection of suitable host cells, such as methylglyoxal over-producing host cells or mutants which steer metabolism toward the production of 1,2-PD rather than other metabolites, can be utilized.

The invention is also drawn to a synthetic operons for transforming a host cell. When incorporated into a host cell, the operon directs the transformed host to produce enzyme activity which converts MG to 1,2-PD and may optionally include genetic elements to increase MG production or to increase the reducing power of the cell. Preferably, the operon includes one or more genes which encode enzymes necessary for expression of aldose reductase activity or glycerol dehydrogenase activity and one or more genes for increased production of MG in the host cell. The operon further includes upstream and/or downstream regulatory elements to control the expression of the gene products(s).

The synthetic operon sequence can be incorporated into any number of suitable and well-characterized plasmid vectors for incorporation into prokaryotic or eukaryotic host cells.

A major advantage of the present invention is that microbial fermentation provides a clean and "environmentally friendly" synthetic route to 1,2-PD. The microbial process uses as a substrate a renewable sugar such as glucose or xylose (found in agricultural crops) or lactose (found in dairy industry wastes). Suitable sugars are also produced in commodity amounts from corn and sugar cane and from lignocellulosic biomass.

Also, the microbial process produces no toxic wastes. The byproducts of fermentation are carbon dioxide, alcohols, and organic acids, all of which can be purified as valuable co-products or used as animal feed.

Another distinct advantage of the invention is that it provides a unique route to 1,2-PD from common sugars, a cheap, renewable, and readily available resource.

A further advantage of the present invention is that microbial processes are straightforward to operate and do not involve high temperatures and pressures. Large fermentation facilities such as those used for the production of ethanol can be readily adapted to the production of 1,2-PD.

Another advantage of the invention is that while MG is toxic to cells, by promoting overexpression of recombinant reductase activities, the recombinant cells remain viable and vigorous under conditions that promote MG production. In other words, any potentially toxic excess of MG produced in the recombinant host cell is rapidly converted to 1,2-PD by the recombinant reductase activity (or activities). The 1,2-PD formed is then exported from the cell.

The maximum theoretical yield of 1,2-PD from sugars is favorable: up to 1.5 moles 1,2-PD per mole sugar. And, unlike n-butanol, 1,2-PD itself has very low toxicity to microorganisms. This allows for good cellular growth and viability at high final product titers. Cellular growth at 100 g/L 1,2-PD has been obtained.

DETAILED DESCRIPTION OF THE INVENTION

Overview

Figure 1:
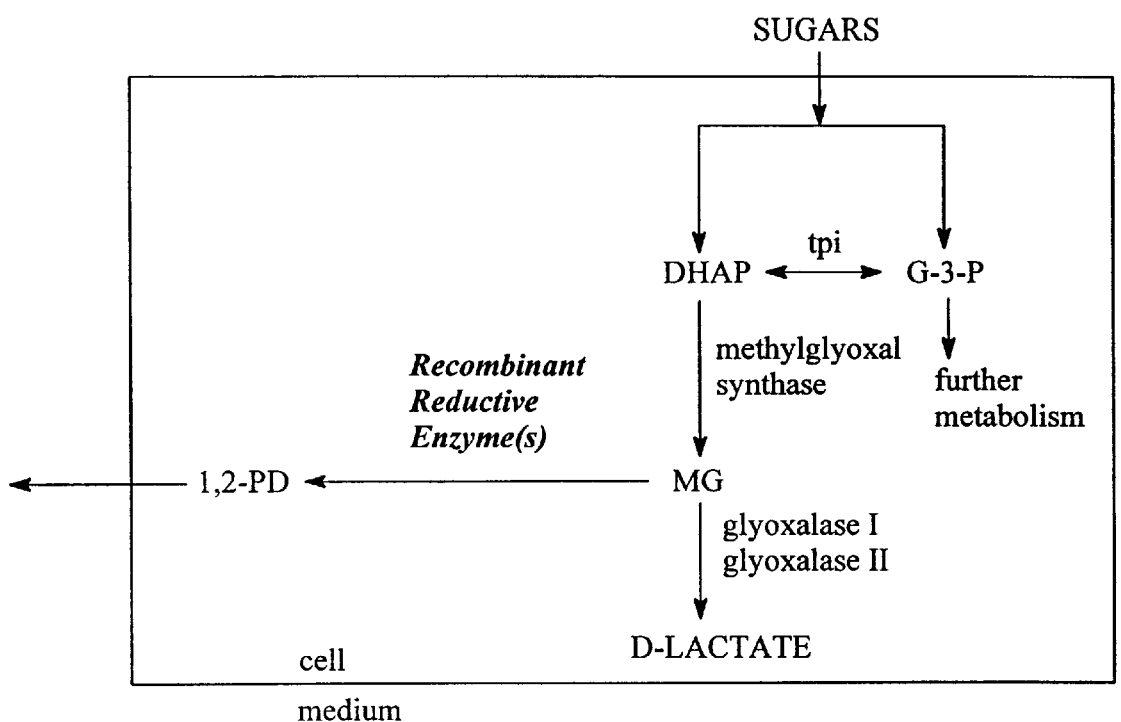
FIG. 1 is a schematic diagram showing the metabolic production of 1,2-PD according to the present invention.

An abbreviated schematic diagram of standard sugar metabolism, as well as the pathway for 1,2-PD production according to the present invention, are shown in FIG. 1. In non-transformed E. coli, sugars are converted to dihydroxyacetone phosphate (DHAP) and glyceraldehyde-3-phosphate (G-3-P) by glycolytic enzymes common to most organisms. The G-3-P is converted to metabolic byproducts such as ethanol, acetate, and succinate, and is also used for further metabolism.

DHAP is the initial intermediate in the 1,2-PD pathway. DHAP is converted to MG by methylglyoxal synthase. In non-transformed cells, the MG is metabolized to D-lactate as indicated in FIG. 1.

E. coli does not make 1,2-PD from sugars that are readily available. By manipulating various metabolic pathways leading both to and from MG, a microorganism can be made to produce 1,2-PD. While not being limited to any particular mode of action, it is thought that this reductive conversion takes place in two steps: 1) reduction of MG to acetol or lactaldehyde: and 2) reduction of acetol or lactaldehyde to 1,2-PD. Both reductions can be accomplished by a single enzyme activity or a combination of enzyme activities.

The crux of the invention, therefore, is a method to produce 1,2-PD using microorganisms which express enzyme activities whereby the microorganisms convert MG into 1,2-PD. The 1,2-PD so formed may then be harvested from the cell media. The microorganisms can be genetically altered organisms, including mutants or other recombinant strains.

The first step of the process is to identify and/or obtain the DNA sequences which encode the desired enzymes and insert or over-express them in the microorganism. This can be accomplished by any means known to the art.

For recombinant microorganisms, the preferred enzymes for the production of 1,2-PD are aldose reductase, glycerol dehydrogenase, or both. The preferred form of the aldose reductase gene is rat lens aldose reductase. The preferred form of the glycerol dehydrogenase gene is *E. coli* glycerol dehydrogenase. (In wild-type *E. coli*, glycerol dehydrogenase is regulated to prevent its catalyzing the conversion of MG to 1,2-PD.)

It must be noted, however, that because the aldose reductase sequence is highly conserved, the source of the aldose reductase gene is not critical to the present invention. (See, for instance, Sato et al. (1995) and Old et al. (1990)). Likewise, the source of the glycerol dehydrogenase gene is not critical to the success of the present invention, so long as the gene product displays the required reductive activity. The invention can be successfully practiced with any gene sequence whose expressed gene product provides reductive activity for the conversion of MG to 1,2-PD.

The rat lens aldose reductase gene has been cloned and sequenced and is available from the U.S. National Institutes of Health or can be obtained as described in Sato et al. and Old et al., supra. Other aldose reductase gene sequences are available from "GENBANK" and can be synthesized or sub-cloned using any of several well known methods. Likewise, genes for glycerol dehydrogenase activity are known ("GENBANK").

The gene which encodes the enzyme having the required activity is then incorporated into a suitable vector which is used to transform a suitable cellular host. The preferred vector is a plasmid vector. The preferred host is a bacterial host, most preferably *E. coli*, although yeast such as *S. cerevisiae* can be utilized with equal success.

Incorporation of the gene into a plasmid transformation or shuttle vector is accomplished by digesting the plasmid with suitable restriction endonucleases, followed by annealing the gene insert to the plasmid "sticky ends," and then ligating the construct with suitable ligation enzymes to re-circulize the plasmid. Each of these steps is well known to those skilled in the art and need not be described in detail here. (See, for instance, Sambrook, Fritsch, and Maniatis (1986), *Molecular Cloning, A Laboratory Manual,* 2nd Ed., incorporated herein by reference for its teaching of vector construction and transformation.)

Once successfully transformed with the required gene(s), the recombinant microorganisms produce 1,2-PD from the fermentation of all common sugars, including arabinose, fructose, galactose, glucose, lactose, maltose, sucrose, and xylose. Additionally, it has been shown that fermentation conditions which increase the formation of MG result in increased titers of 1,2-PD.

For purposes of this invention, increased MG production in the host cell can be obtained using any method now known or developed in the future. In *E. coli*, methods to obtain increased MG production include, but are not limited to: culturing under low-phosphate (Ferguson et al. (1996)), culturing with cyclic AMP and pentoses such as xylose or arabinose (Ackerman et al. (1974)), increasing intracellular DHAP (e.g. by culturing a triose phosphate isomerase knockout mutant), increasing conversion of DHAP to MG (e.g. by over-expressing methylglyoxal synthase), and culturing under unregulated metabolism. (See, for instance, Freedberg et al. (1971) and Kadner et al. (1992).)

Similarly, by utilizing MG over-producing mutants as the host, or by over-expressing endogenous genes (or by introducing exogenous genes) which promote the production of MG, production of 1,2-PD from the transformed cells is maximized.

Careful selection of mutant hosts can also be used to increase the yield of 1,2-PD. *E. coli* mutants, such as AA200 (a triose phosphate isomerase knockout mutant, *E. coli* Genetic Stock Center, New Haven, Conn., U.S.A.), can be used as host cells to increase the intracellular levels of MG, thereby increasing 1,2-PD production. Similarly, glyoxalase knockout mutants can also be used as host cells, thereby increasing the intracellular level of MG for conversion to 1,2-PD Appropriate host selection (using other *E. coli* mutants) also allows the conditions under which 1,2-PD is produced to be varied, e.g., aerobic or anaerobic production, different sugars as a carbon source, etc. For example, when transformed to express exogenous aldose reductase, the *E. coli* strain AA200 noted above has been shown to convert many sugars, including galactose, lactose, and sucrose, into 1,2-PD under aerobic conditions. Analogous transformations can also be accomplished in other host organisms, such as yeast.

Isolation of the 1,2-PD formed from the cell medium can be accomplished by any means known in the separation art. The preferred method is to filter the culture medium to separate cells and cellular debris, and then to isolate the 1,2-PD from the medium by vacuum distillation. (See, for instance, Simon et al. (1987).) If so desired, the recombinant microorganisms may be completely lysed by any known means prior to isolation of the 1,2-PD.

*E. coli* Transformed with pKKARX

For purposes of brevity and clarity only, the following description is limited to a transformation construct containing an aldose reductase gene. The identical procedure can be followed to insert any gene sequence having the proper activity, Such as glycerol dehydrogenase, into a host to thereby enable or maximize the production of 1,2-PD. Other enzymes which promote production of 1,2-PD include: carbonyl reductase (*E. coli* 1.1.1.84), glycerol dehydrogenase (*E. coli* 1.1.1.6, *E. coli* 1.1.1.156), aldehyde reductase (*E. coli* 1.1.1.2), methylglyoxal reductase (also known as 2-oxoaldehyde reductase and lactaldehyde dehydrogenase, *E. coli* 1.1.1.78), L-glycol dehydrogenase (*E. coli* 1.1.1.185), alcohol dehydrogenase *E. coli* 1.1.1.1, *E. coli*

1.1.1.2), 1,2-PD dehydrogenase, (lactaldehyde reductase, *E. coli* 1.1.1.55), and 1,2-PD oxidoreductase, (lactaldehyde reductase, *E. coli* 1.1.1.77).

Any *E. coli* strain can be transformed to contain the aldose reductase insert described herein. The preferred strain is *E. coli* AG1 (F–, endA1, hsdR17, {kn⁻, mk⁺} supE44, thi⁻1, recA1, gyrA96 relA1, λ⁻), available commercially from Stratagene Corporation (La Jolla, Calif.). This strain was used as the host strain for 1,2-PD production in the Examples described below unless otherwise noted. The AA200 and K10 strains were obtained from the *E. coli* Genetic Stock Center (New Haven, Conn.).

Similarly, any yeast strain can be transformed to contain the desired gene insert. *S. cerevisiae*, numerous strains of which are available from a host of commercial suppliers and the American Type Culture Collection, is preferred.

For transformation of bacteria, a plasmid vector containing the gene insert is preferred. Several suitable vectors are available commercially or can be obtained by methods well known to the art. A preferred expression vector is pKK233-2, available commercially from the Pharmacia Biotech (Piscataway, N.J.). The sequence of the pKK233-2 vector is shown in SEQ. ID. NO: 1. Suitable restriction enzymes and T4 DNA ligase to manipulate the vector can be obtained from several international suppliers, including Promega Corporation, (Madison, Wis.) and New England Biolabs (Beverly, Mass.).

The nucleotide sequence of the preferred rat lens aldose reductase gene is shown in SEQ. ID. NO: 3. The amino acid sequence of the encoded aldose reductase enzyme is shown in SEQ. ID. NO: 4.

The aldose reductase gene is inserted into the pKK233-2 plasmid (SEQ. ID. NO: 1) following standard procedures. (This process is essentially identical to that described by Old et al. (1990).) The resulting construct is designated pKKARX. The starting pKK233-2 plasmid is designed for direct cloning of eukaryotic genes in *E. coli*. The plasmid contains the highly expressed trc promoter (17 base pair spacing between the trp-35 region and the lac UV5-10 region), the lacZ ribosome binding site, and an ATG initiation codon. To prevent unstable replication, the strong rrnB transcription terminator has been introduced downstream of the Multiple Cloning Site. Digestion with NcoI exposes the start codon for direct ligation and expression of foreign proteins. Eukaryotic gene fragments lacking a prokaryotic ribosome binding site and/or an ATG can be inserted in the correct reading frame by using one of several commercially available NcoI linkers. (Available, for instance, from Pharmacia Biotech, Piscataway, N.J.). The NcoI recognition sequence, CCATGG, commonly occurs at the initiation codon of eukaryotic genes, allowing direct ligation to the vector.

*E. coli* can then be transformed using the pKKARX construct. All transformations described herein were performed by the calcium chloride method using standard and well-known methodologies. While the calcium chloride method is preferred, transformation can be accomplished with equal success using any of several conventional procedures, such as electroporation and the like.

Once transformed with pKKARX, wild-type *E. coli* host cells produce 1,2-PD from arabinose, glucose, and xylose. Analysis for production of 1,2-PD is performed as described in Example 1, below.

*E. coli* Transformed with pSEARX

Another aspect of the invention is to transform the host with an insert which includes inducible or repressible genetic elements. This allows the production of 1,2-PD to be switched on or off by addition of a suitable inducer or repressor.

The preferred construct, designated pSEARX, is constructed by digesting pKKARX (described above) and a commercially-available vector designated pSE380 (Invitrogen, La Jolla, Calif.) with NcoI and EcoRI. The resulting fragments from NcoI and EcoRI digestion are then separated by agarose gel electrophoresis, and the aldose reductase gene and pSE380 vector purified using "GENECLEAN" (Bio 101 Inc., La Jolla, Calif.) according to the manufacturer's instructions. The two fragments are then ligated and transformed into AG1 using standard procedures (Sambrook et al., supra).

Figure 2:
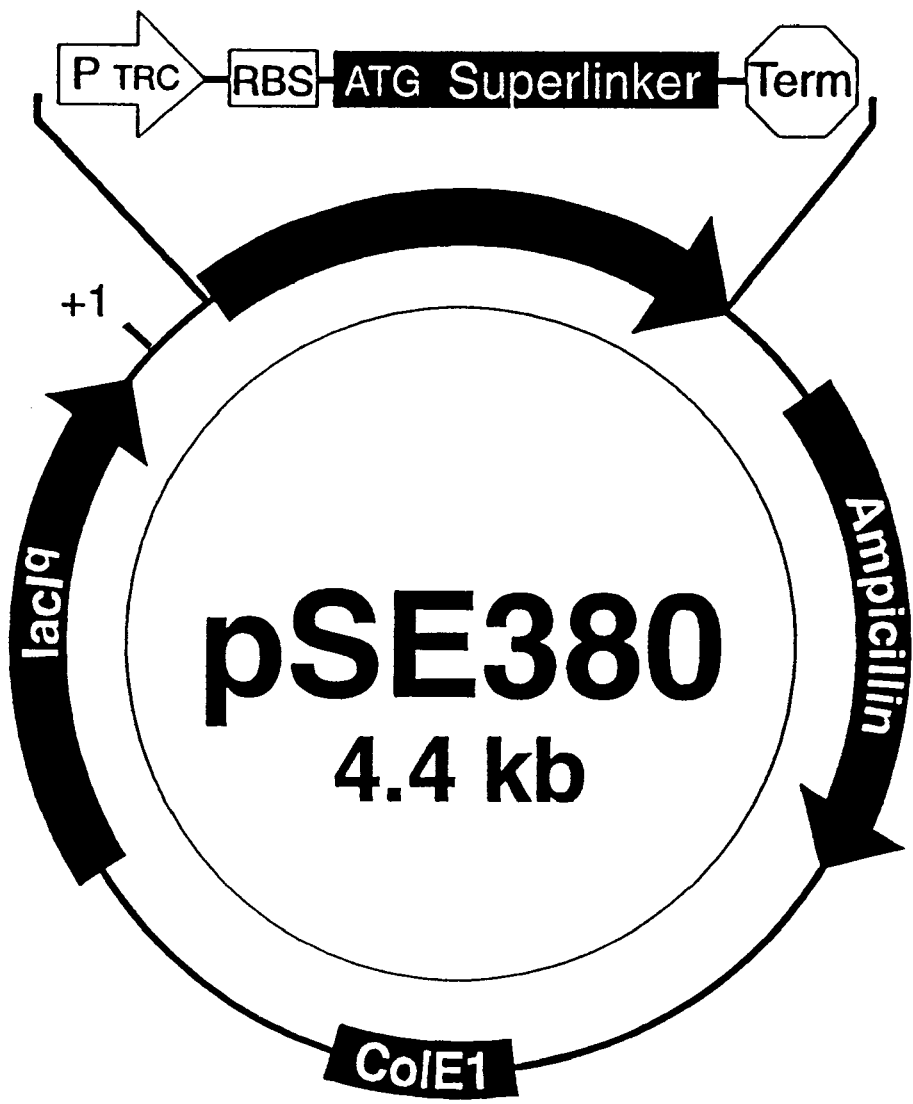
FIG. 2 is a schematic diagram of a preferred repressible transformation vector for use in the present invention, pSE380.

A schematic of the starting pSE380 plasmid is shown in FIG. 2. The pSE380 plasmid includes a strong trc promoter for high level transcription, as well as the lacO operator and lacI$^q$ repressor gene (which allows transcriptional regulation in any *E. coli* strain). While the pSE380 starting plasmid is preferred, any construct containing an inducible or repressible promoter which can control the expression of gene sequences operationally linked to the promoter will function with equal success. In addition to the trc promoter, examples of well known promoters which can be utilized include lac, tac, and phoA. The nucleotide sequence of pSE380 is given in SEQ. ID. NO: 2.

Inducing a wild-type *E. coli* host transformed with pSEARX by adding IPTG to the media results in the production of 1,2-PD when the host is grown on arabinose, glucose, and xylose.

Mutant Host Selection to Maximize Utilizable Substrates and 1,2-PD Production

Increased flexibility when producing 1,2-PD from transformed *E. coli* or yeast is afforded by selection of a suitable mutant host. For instance, when transformed with either pKKARX or pSEARX as described above, triose phosphate isomerase knockout mutant bacteria, such as *E. coli* strain AA200, produce 1,2-PD when fermented with any combination of arabinose, galactose, glucose, lactose, sucrose, and xylose. Triose phosphate isomerase catalyzes the interconversion of DHAP to G-3-P. (See FIG. 1.) By utilizing a host mutant which lacks triose phosphate isomerase activity, the metabolic fate of DHAP is directed to the formation of MG, which is then converted by various reductive enzyme activities into 1,2-PD, thereby increasing 1,2-PD titers.

Likewise, 1,2-PD production can be maximized by utilizing other mutants lacking one or more enzymes which decrease intracellular pools of MG. For instance, the normal metabolic pathway to detoxify intracellular methylglyoxal utilizes glyoxalase I. Glyoxolase I catalyzes the conversion of MG to S-D-lactoylglutathione, which is subsequently converted to lactate by glyoxalase II. Consequently, when a host is transformed to express a recombinant enzyme having MG reducing activity, the MG-reducing enzyme competes with glyoxalase I for the available MG. By utilizing glyoxalase I knockout mutants, the intracellular pool of MG for conversion to 1,2-PD is increased, and the ultimate production of 1,2-PD is likewise increased.

Glyoxalase mutants can be constructed in *E. coli*, yeast, or any other suitable host, using standard techniques. Because several glyoxalase oligonucleotide sequences are known ("GENBANK"), the most straightforward route to obtain a glyoxalase mutant is to recombine a deletion into the chromosomal copy of the glyoxalase gene whereby glyoxalase activity is destroyed. An example of how this can be done is described in Koob et al. (1994).

Negative Controls

To provide a negative control for the pKKARX and pSEARX constructs, a plasmid designated pKKARX/PstI was constructed by digesting pKKARX with PstI and purifying the vector portion of the resulting digest. The vector was then self-ligated resulting in an approximately 1 kb deletion within the aldose reductase gene on the plasmid. AG1 cells transformed with pKKARX/Pst show no aldose reductase activity or 1,2-PD production.

Yeast Hosts

In an analogous fashion, yeast (as well as other cellular hosts) can be transformed to contain the aldose reductase gene (or any of the other genes listed above) and can be used to produce 1,2-PD by fermentation of common sugars.

In yeast, the aldose reductase gene is first inserted into an appropriate shuttle vector. In the preferred embodiment, an aldose reductase cassette is ligated into YpJ66 digested with EcoRI/KpnI, thus replacing the galK cassette with an aldose reductase cassette between EcoRI and KpnI. YpJ66 is constructed from YEp352, whose oligonucleotide sequence is shown in SEQ. ID. NO: 5, and can be constructed according to the method of Hill et al. (1986). In short, this is accomplished by inserting the CUP1 promoter, (galK) and CYC1 terminator sequence into the XbaI site of Yep352.

Preferably, the vector is then transformed into YPH500 (ATCC 76626) (leu⁻, trp⁻, ura⁻, lys⁻, ade⁻, his⁻) by standard methods and fed the required amino acids for growth, except uracil, which is used as the marker to maintain the plasmid in yeast. In the same fashion as transformed *E. coli*, yeast transformed to contain the aldose reductase insert produce 1,2-PD in isolatable quantities when fermented on a wide variety of common sugars, including galactose, glucose, sucrose, fructose, and maltose.

Other genetically altered strains can produce 1,2-PD when cultured on other sugar carbon sources such as xylose and lactose.

Synthetic Operons for the Production of 1,2-PD

Ideally, three criteria should be maximized in order to maximize production of 1,2-PD. These three criteria are: increased production of MG, increased production of enzymes to convert MG to 1,2-PD, and increased production of enzymes such as pyridine nucleotide transferase to increase the reducing power within the cell (and thereby favor the reduction of MG to 1,2-PD). In this embodiment of the invention, a methylglyoxal synthase gene for increasing production of MG, and/or an aldose reductase or glycerol dehydrogenase gene for converting MG to 1,2-PD, and/or a pyridine nucleotide transferase gene for increasing the reductive power of the host cell are operationally linked, in any order, under the control of one or more promoters, to yield a synthetic operon which maximizes the production of 1,2-PD in host microorganisms transformed with the operon.

The methylglyoxal synthase gene has been cloned and expressed in *E. coli* and is shown in SEQ. ID. NO: 6. The ATG initiation codon is underlined. (See also Percy and Harrison (1996)). Likewise, the pyridine nucleotide transferase gene, encoding subunits A and B, is also known and is shown in SEQ. ID. NO: 7. The amino acid sequences of the encoded A and B subunits of pyridine nucleotide transferase are shown in SEQ. ID. NO: 8 and SEQ. ID. NO: 9, respectively. The glycerol dehydrogenase gene has also been identified; its oligonucleotide sequence is shown in SEQ. ID. NO: 10. The glycerol dehydrogenase amino acid sequence is shown in SEQ. ID. NO: 11.

To construct the synthetic operon according to the present invention, SEQ. ID. NO: 3 (aldose reductase), SEQ. ID. NO: 6 (methylglyoxal synthase), SEQ. ID. NO: 7 (pyridine nucleotide transferase) and/or SEQ. ID. NO: 10 (glycerol dehydrogenase) are operatively linked together in a 5' to 3' orientation. The order of the genes is not critical to the functionality of the operon, so long as each gene is operationally linked to its neighbor in a 5' to 3' orientation.

The gene sequences are inserted into a suitable plasmid host which includes one or more promoter sequences such that the promoter is operationally linked to the gene sequences and can function to promote or repress transcription of the genes. Suitable promoter sequences include any number of well known and widely used promoters such as lac, trc, tac, and phoA. For instance, pSE380 contains the trc promoter. A very large number of suitable transformation vectors containing the above-listed promoters are commercially available from several international suppliers.

The gene insert containing the functional genes is constructed by standard and well known means. In short, the individual gene inserts are digested with an appropriate restriction enzyme to yield complimentary "sticky ends," which are then annealed to one another and ligated with T4 ligase. The gene construct is then again digested to yield appropriate complimentary ends to be operationally inserted into a plasmid vector containing the promoter sequences. Many commercial plasmids contain a Multiple Cloning Site which allows any number of different restriction enzymes to be utilized to effect insertion of the construct into the plasmid vector. The vector is then used to transform a suitable host, as described above.

When transformed with the synthetic operon as described herein, the recombinant microorganism produces 1,2-PD in isolatable quantities.

The synthetic operon need not contain any or all of the above-noted genes. At a minimum, at least one gene encoding an enzyme to effect the reduction of MG to 1,2-PD must be present, such as the aldose reductase gene or the glycerol dehydrogenase gene or some other gene or genes. In addition, either or both of the methylglyoxal synthase and pyridine nucleotide transferase genes may be present. Additionally, the genes need not all be under the control of a single promoter. For purposes of flexibility, each individual gene can be placed under the control of a separate promoter.

Additionally, an alternative to utilizing a triose phosphate isomerase knockout mutant host strain is to place the triose phosphate isomerase gene under the control of a promoter sequence. This enables transcription of the gene to be switched on or off, depending upon the conditions present. To effect insertion of promoter sequence in operational orientation to the triose phosphate isomerase gene, standard recombinant genetic techniques are utilized. (Again, see Sambrook, Fritsch, and Maniatis (1986), *Molecular Cloning, A Laboratory Manual, 2nd Ed.*) The promoter of interest is placed into a suitable vector, preferably a plasmid vector, which contains appropriate cloning sequences to enable operational insertion of the promoter sequence into the genome of the host organism. Successful incorporation of the plasmid is determined via antibiotic resistance and/or testing for induction (or repression) of triose phosphate isomerase. Such method are well known to those skilled in the art.

EXAMPLES

The following Examples are included solely for illustrative purposes to provide a more complete understanding of the invention. The Examples do not limit the scope of the invention disclosed or claimed herein in any fashion.

Example 1

Chromatographic Analysis of Culture Broth

Figure 3:
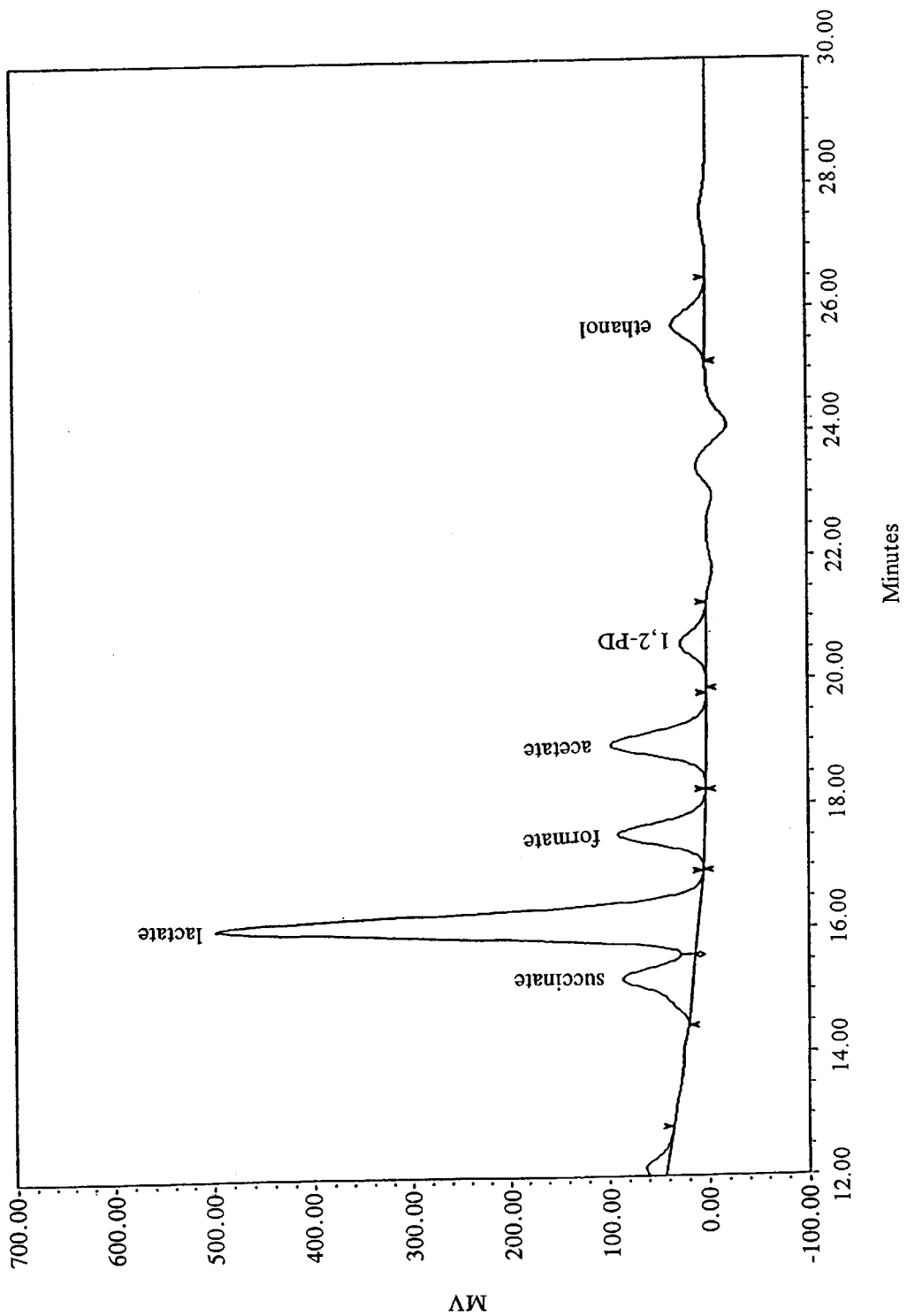
FIG. 3 is an HPLC elution profile of media from recombinant E. coli strain AG1 cells which express exogenous aldose reductase activity showing production of 1,2-PD.
Figure 4:
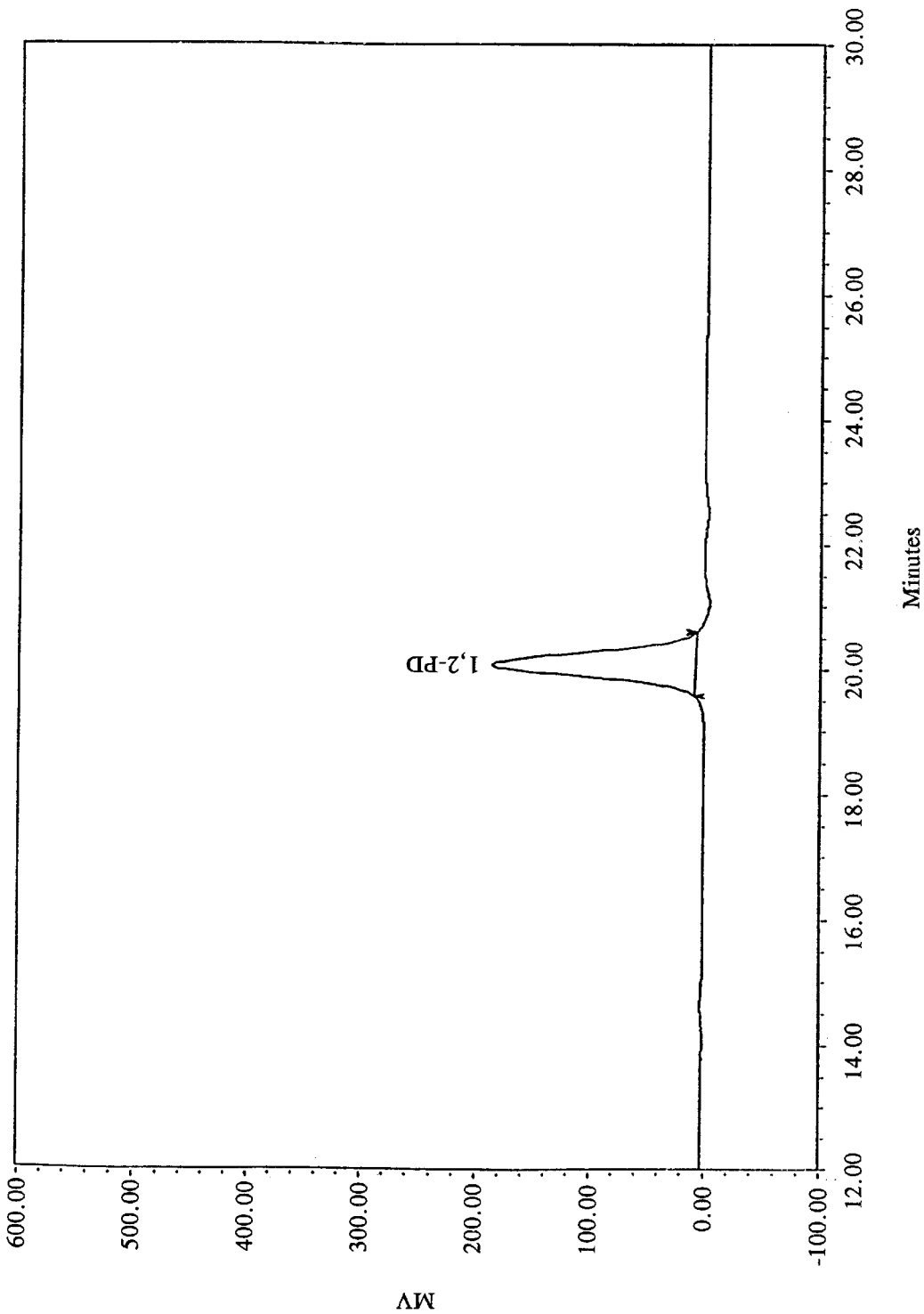
FIG. 4 is an HPLC elution profile of a 1,2-PD standard.
Figure 5:
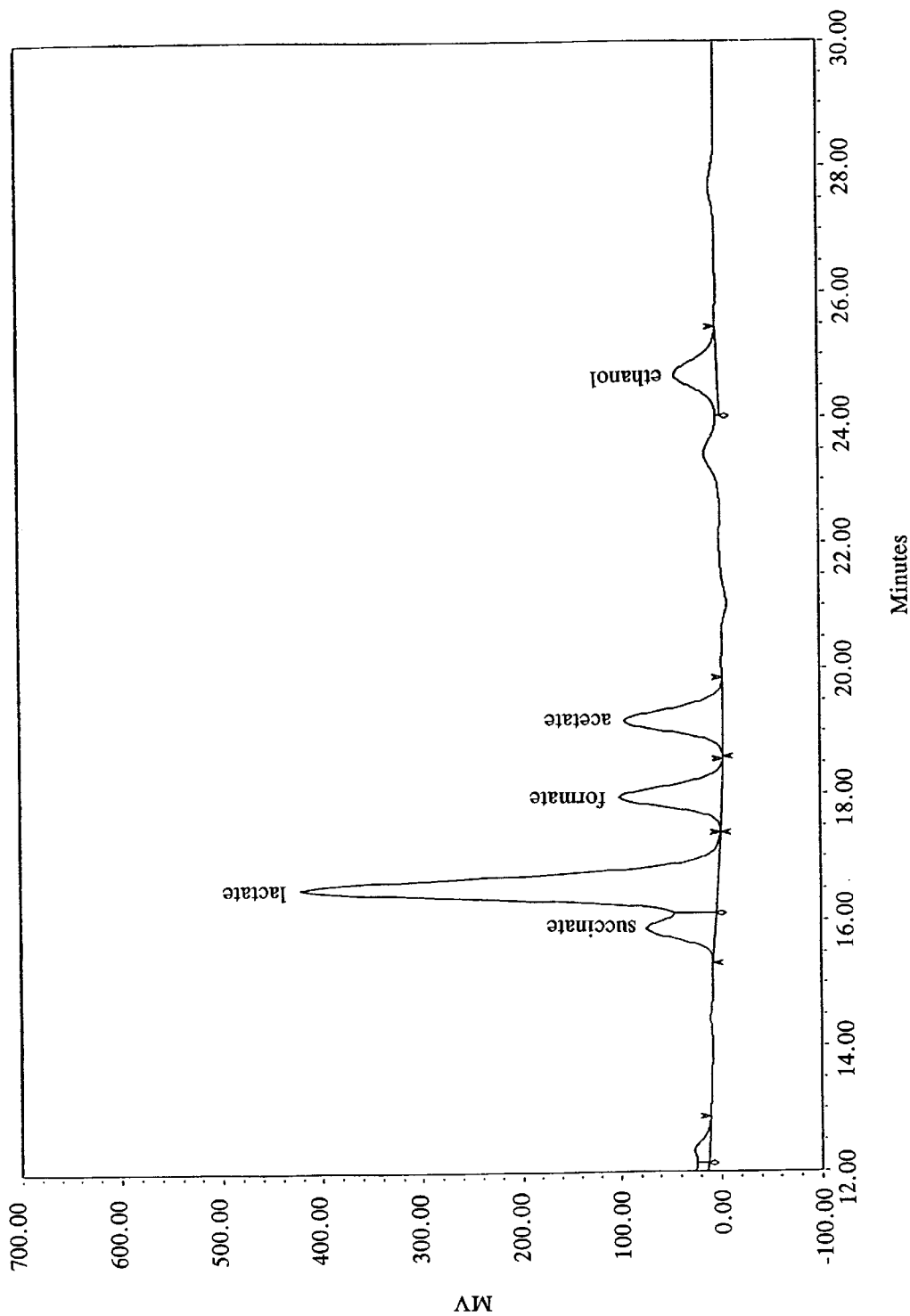
FIG. 5 is an HPLC elution profile of media from wild-type E. coli showing no production of 1,2-PD.

FIGS. 3 and 5 depict HPLC analyses of the culture broth of an *E. coli* strain AG1 transformed to express aldose reductase (using pKKARX) and a non-transformed culture of the same strain, respectively. FIG. 4 depicts an HPLC elution profile of a 1,2-PD standard solution. With reference to FIGS. 3 and 5, the fermentations were performed under standard anaerobic conditions using 5 g/L glucose as carbon source. Media samples were centrifuged and filtered before analysis.

To generate the plots shown in FIGS. 3 and 5, an organic acids column (Bio-Rad "HPX87H", Hercules, Calif.) was used to quantify 1,2-PD, ethanol, sugars, and organic acids under the following conditions: 50 μL sample size, pH 2 ($H_2SO_4$); 0.5 mL/min flow rate, and 40° C. column temperature. Peaks were detected by a refractive index detector at 40° C.

The 1,2-PD peak from the organic acids column was further analyzed by injection onto a cation-exchange column (Waters "SUGAR-PAK II," Marlboro, Mass.). The 1,2-PD peak isolated from the fermentation broth elutes at exactly the same time as the 1,2-PD control. The secondary peak identifications were performed on the "SUGAR-PAK II" column under the following conditions: 50 μL sample size, Milli-Q water mobile phase; 0.5 mL/min flow rate; and 90° C. column temperature.

Additionally, analyses were performed in which the 1,2-PD peak from the organic acids column was collected and subjected to gas chromatographic (GC) analysis and mass spectrographic analysis. The GC peak co-eluted with the 1,2-PD standard. Mass spectrometry showed the same fragmentation patern as the 1,2-PD standard. The fact that the same peak co-eluted with a 1,2-PD standard on 3 different columns (HPLC organic acids column, HPLC sugars column, and GC), with different methods of separation, as well as its fragmentation in mass spectrography, its identification as 1,2-PD is quite certain.

Example 2

Production of 1,2-Propanediol from Various Common Sugars

In this Example, a triose phosphate isomerase mutant (tpi−), AA200, was transformed with pSEARX containing the gene for aldose reductase as described above. (This transformed cell line is designated AA200::pSEARX). The non-transformed AA200 mutant yields higher intracellular concentrations of methylglyoxal, the precursor to 1,2-PD, than the wild-type. (See Hopper and Cooper (1972).) When transformed with pSEARX, the AA200::pSEARX cell line produced 1,2-PD from arabinose, galactose, glucose, lactose, sucrose, and xylose. The yield of 1,2-PD from AA200::pSEARX fermented with various sugars was as follows:

TABLE 1

| SUGAR | TITER 1,2-PD, mg/L |
|---|---|
| Galactose | 66 |
| Glucose | 71 |
| Lactose | 6 |
| Sucrose | 7 |
| Xylose | 49 |

Fermentation was performed using standard anaerobic fermentation procedures using 10 g/L of the appropriate sugar. The fermentation was allowed to proceed for 24 hours prior to analysis for 1,2-PD.

Example 3

Inducible Production of 1,2-PD

Figure 6:
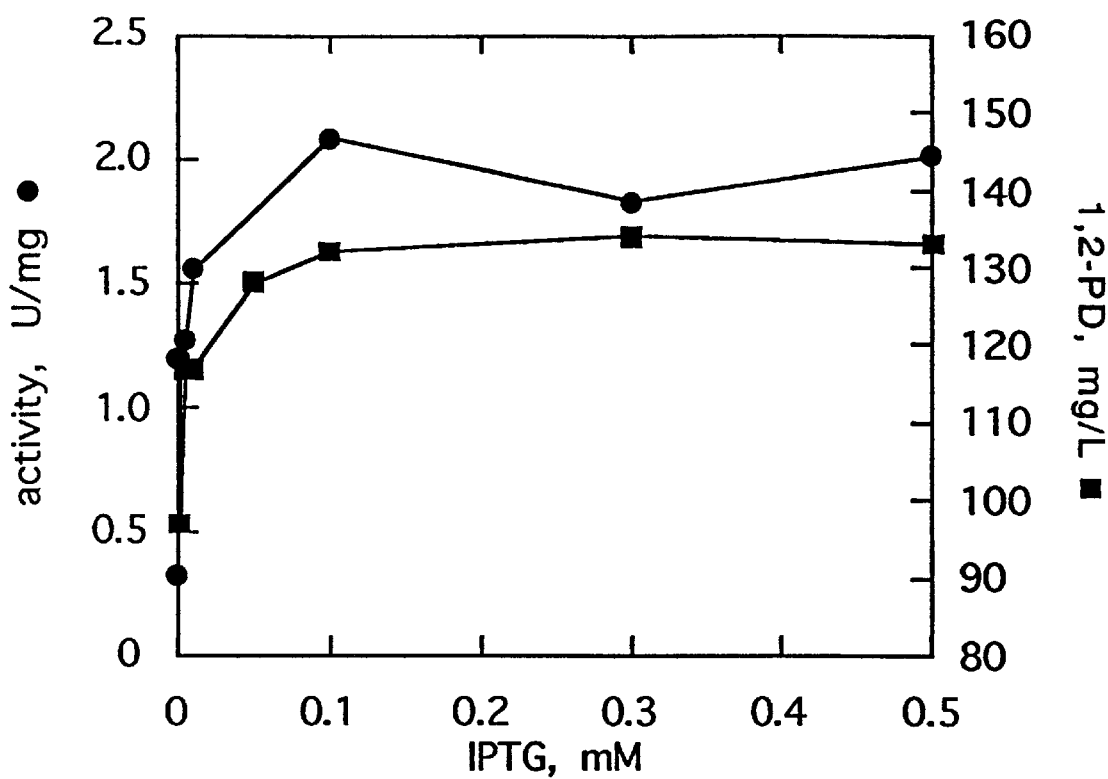
FIG. 6 is a graph depicting inducible production of 1,2-PD from recombinant E. coli containing an operon for the production and regulation of aldose reductase according to the present invention. Aldose reductase production was induced by the addition of IPTG to the culture medium.

In this Example, the results of which are depicted in FIG. 6, E. coli strain AG1 was transformed as described herein with the pSEARX plasmid containing the aldose reductase gene. The transformed cells were then cultured under standard anaerobic conditions on 5 g/L glucose with increasing levels of the promoter IPTG. The X-axis of FIG. 6 gives the concentration of IPTG in millimolarity. The right-hand Y-axis (■) reports the production of 1,2-PD in mg/L as a function of IPTG concentration. Likewise the left-hand Y-axis (●) reports the activity of aldose reductase in U/mg. As is clearly shown in FIG. 6, inducing the promoter leads to the production of 1,2-PD.

Example 4

Inhibition of Cell Growth by 1,2-PD

Figure 7:
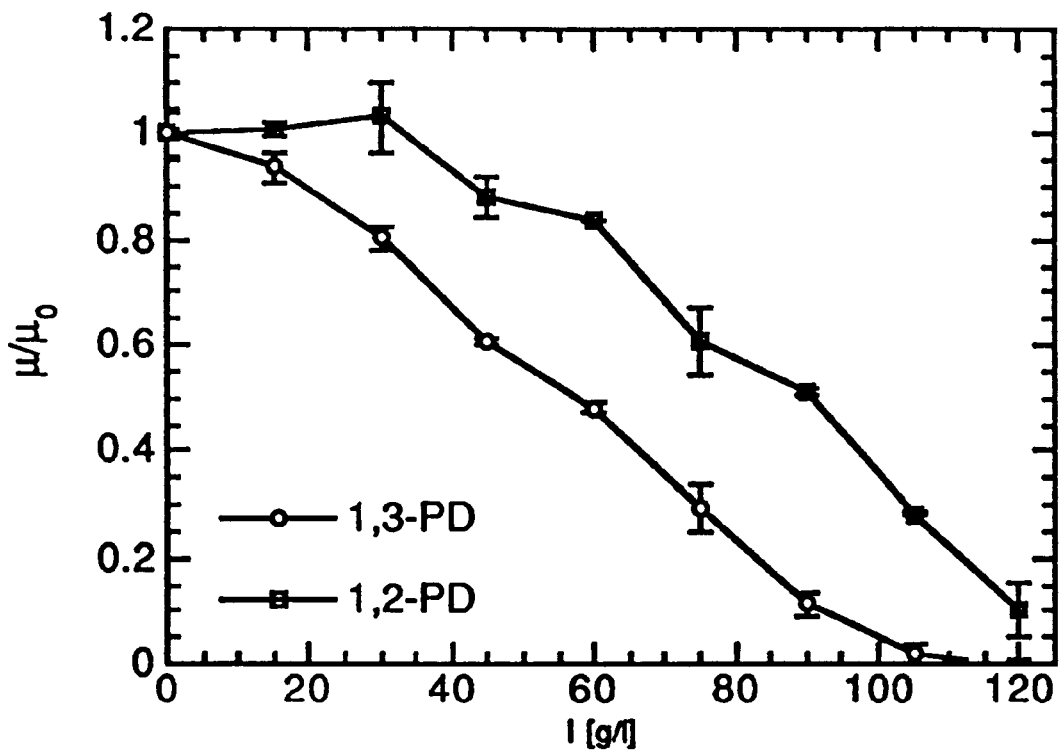
FIG. 7 is a graph depicting the inhibition of cell growth due to the presence of 1,2-PD and 1,3-PD. As shown in the graph, 1,2-PD does not result in complete inhibition of cell growth until the amount added to the culture media is approximately 120 g/L.

Here, an Experiment was performed to determine at what level the presence 1,2-PD and 1,3-PD begin to have an adverse effect on E. coli cell growth. Anaerobic batch cultivations of E. coli were carried out in 10 mL culture tubes. Nine different batch cultivations, covering a range between 0 and 120 g/L of 1,2-PD (○) and and 1,3-propanediol (□) were carried out in triplicate. Using optical density measurements, the growth in each tube was monitored and the specific growth rate determined. The results are depicted in FIG. 7. The ratio $\mu/\mu_0$ has been plotted as a function of the concentration of 1,2-PD and 1,3-PD (I, g/L). The value of $\mu$ equals the specific growth rate determined for the corresponding concentration of 1,2 or 1,3-PD; the value of $\mu_0$ equals the specific growth rate determined in the absence of any 1,2-PD or 1,3-PD. The error bars indicate the standard deviation between the triplicate experiments. As can be seen from FIG. 7, 1,2-PD does not cause complete inhibition of cell growth until a concentration of approximately 120 g/L is reached.

Example 5

Anaerobic Production of 1,2-PD Utilizing Recombinant Glycerol Dehydrogenase Gene E. coli strain AG1 was transformed in standard fashion with pSE380 containing a gene for E. coli glycerol dehydrogenase. The plasmid, designated pNEA10, was constructed in standard fashion. The transformed cells were then cultured under strictly anaerobic conditions on 10 g/L glucose. The fermentation was allowed to proceed for 12 hours to allow cell growth prior to addition of IPTG. The fermentation was then allowed to proceed for an additional 24 hours prior to analysis for 1,2-PD. The results are shown in Table 2:

TABLE 2

| plasmid | IPTG mM | 1,2-PD Titer mg/L | Activity* U/mg |
|---|---|---|---|
| pSE380† | 0.0 | 0 | 0.10 |
| pNEA10 | 0.0 | 100 | 0.48 |
| pNEA10 | 0.05 | 190 | 3.00 |
| pNBA10 | 0.10 | 220 | 2.70 |
| pNEA10 | 0.25 | 220 | 3.10 |

*measured using glycerol as a substrate
†control plasmid without glycerol dehydrogenase gene

Example 6

Production of 1,2-PD by Host Containing Recombinant Glycerol Dehydrogenase Gene in Combination with Promoter

*E. coli* strain AG1 was transformed as described in Example 5. The transformed cells were then cultured on 15 g/L glucose under anaerobic conditions. Prior to the fermentation, the media was not purged of oxygen. IPTG was added at the start of the fermentation. The fermentation was allowed to proceed for 36 hours prior to analysis for 1,2-PD. The results are depicted in Table 3:

TABLE 3

| plasmid | IPTG mM | 1,2-PD Titer mg/L | Activity* U/mg |
|---------|---------|-------------------|----------------|
| pSE380† | 0.0     | 0                 | 0.10           |
| pNEA10  | 0.0     | 30                | 2.31           |
| pNEA10  | 0.05    | 100               | 9.89           |

*measured using acetol as a substrate
†control plasmid without glycerol dehydrogenase gene

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 4593 base pairs
      (B) TYPE: nucleic acid
      (C) STRANDEDNESS: single
      (D) TOPOLOGY: circular (ii) MOLECULE TYPE: DNA (genomic)

(iii) HYPOTHETICAL: NO (iv) ANTI-SENSE: NO (vi) ORIGINAL SOURCE:
      (A) ORGANISM: Vector pKK232-2

(xi) SEQUENCE DESCRIPTION: SEQ ID NO:1:

```
CCGGATCCTC TACGCCGGAC GCATCGTGGC CGGCATCACC GGCGCCACAG GTGCCGTTGC        60

TGGCGCCTAT ATCGCCGACA TCACCGATGG GGAAGATCGG GCTCGCCACT TCGGGCTCAT       120

GAGCGCTTGT TTCGGCGTGG GTATGGTGGC AGGCCCCGTG GCCGGGGGAC TGTTGGGCGC       180

CATCTCCTTG CATGCACCAT TCCTTGCGGC GGCGGTGCTC AACGGCCTCA ACCTACTACT       240

GGGCTGCTTC CTAATGCAGG AGTCGCATAA GGGAGAGCGT CGACCGATGC CCTTGAGAGC       300

CTTCAACCCA GTCAGCTCCT TCCGGTGGGC GCGGGGCATG ACTATCGTCG CCGCACTTAT       360

GACTGTCTTC TTTATCATGC AACTCGTAGG ACAGGTGCCG GCAGCGCTCT GGGTCATTTT       420

CGGCGAGGAC CGCTTTCGCT GGAGCGCGAC GATGATCGGC CTGTCGCTTG CGGTATTCGG       480

AATCTTGCAC GCCCTCGCTC AAGCCTTCGT CACTGGTCCC GCCACCAAAC GTTTCGGCGA       540

GAAGCAGGCC ATTATCGCCG GCATGGCGGC CGACGCGCTG GGCTACGTCT TGCTGGCGTT       600

CGCGACGCGA GGCTGGATGG CCTTCCCCAT TATGATTCTT CTCGCTTCCG GCGGCATCGG       660

GATGCCCGCG TTGCAGGCCA TGCTGTCCAG GCAGGTAGAT GACGACCATC AGGGACAGCT       720

TCAAGGATCG CTCGCGGCTC TTACCAGCCT AACTTCGATC ACTGGACCGC TGATCGTCAC       780

GGCGATTTAT GCCGCCTCGG CGAGCACATG GAACGGGTTG GCATGGATTG TAGGCGCCGC       840

CCTATACCTT GTCTGCCTCC CCGCGTTGCG TCGCGGTGCA TGGAGCCGGG CCACCTCGAC       900

CTGAATGGAA GCCGGCGGCA CCTCGCTAAC GGATTCACCA CTCCAAGAAT TGGAGCCAAT       960

CAATTCTTGC GGAGAACTGT GAATGCGCAA ACCAACCCTT GGCAGAACAT ATCCATCGCG      1020

TCCGCCATCT CCAGCAGCCG CACGCGGCGC ATCTCGGGCA GCGTTGGGTC CTGGCCACGG      1080
```

```
GTGCGCATGA TCGTGCTCCT GTCGTTGAGG ACCCGGCTAG GCTGGCGGGG TTGCCTTACT      1140

GGTTAGCAGA ATGAATCACC GATACGCGAG CGAACGTGAA GCGACTGCTG CTGCAAAACG      1200

TCTGCGACCT GAGCAACAAC ATGAATGGTC TTCGGTTTCC GTGTTTCGTA AAGTCTGGAA      1260

ACGCGGAAGT CAGCGCCCTG CACCATTATG TTCCGGATCT GCATCGCAGG ATGCTGCTGG      1320

CTACCCTGTG GAACACCTAC ATCTGTATTA ACGAAGCGCT GGCATTGACC CTGAGTGATT      1380

TTTCTCTGGT CCCGCCGCAT CCATACCGCC AGTTGTTTAC CCTCACAACG TTCCAGTAAC      1440

CGGGCATGTT CATCATCAGT AACCCGTATC GTGAGCATCC TCTCTCGTTT CATCGGTATC      1500

ATTACCCCCA TGAACAGAAA TTCCCCCTTA CACGGAGGCA TCAAGTGACC AAACAGGAAA      1560

AAACCGCCCT TAACATGGCC CGCTTTATCA GAAGCCAGAC ATTAACGCTT CTGGAGAAAC      1620

TCAACGAGCT GGACGCGGAT GAACAGGCAG ACATCTGTGA ATCGCTTCAC GACCACGCTG      1680

ATGAGCTTTA CCGCAGCTGC CTCGCGCGTT TCGGTGATGA CGGTGAAAAC CTCTGACACA      1740

TGCAGCTCCC GGAGACGGTC ACAGCTTGTC TGTAAGCGGA TGCCGGGAGC AGACAAGCCC      1800

GTCAGGGCGC GTCAGCGGGT GTTGGCGGGT GTCGGGCGC AGCCATGACC CAGTCACGTA       1860

GCGATAGCGG AGTGTATACT GGCTTAACTA TGCGGCATCA GAGCAGATTG TACTGAGAGT      1920

GCACCATATG CGGTGTGAAA TACCGCACAG ATGCGTAAGG AGAAAATACC GCATCAGGCG      1980

CTCTTCCGCT TCCTCGCTCA CTGACTCGCT GCGCTCGGTC GTTCGGCTGC GGCGAGCGGT      2040

ATCAGCTCAC TCAAAGGCGG TAATACGGTT ATCCACAGAA TCAGGGGATA ACGCAGGAAA      2100

GAACATGTGA GCAAAAGGCC AGCAAAAGGC CAGGAACCGT AAAAAGGCCG CGTTGCTGGC      2160

GTTTTTCCAT AGGCTCCGCC CCCCTGACGA GCATCACAAA AATCGACGCT CAAGTCAGAG      2220

GTGGCGAAAC CCGACAGGAC TATAAAGATA CCAGGCGTTT CCCCCTGGAA GCTCCCTCGT      2280

GCGCTCTCCT GTTCCGACCC TGCCGCTTAC CGGATACCTG TCCGCCTTTC TCCCTTCGGG      2340

AAGCGTGGCG CTTTCTCATA GCTCACGCTG TAGGTATCTC AGTTCGGTGT AGGTCGTTCG      2400

CTCCAAGCTG GGCTGTGTGC ACGAACCCCC CGTTCAGCCC GACCGCTGCG CCTTATCCGG      2460

TAACTATCGT CTTGAGTCCA ACCCGGTAAG ACACGACTTA TCGCCACTGG CAGCAGCCAC      2520

TGGTAACAGG ATTAGCAGAG CGAGGTATGT AGGCGGTGCT ACAGAGTTCT TGAAGTGGTG      2580

GCCTAACTAC GGCTACACTA GAAGGACAGT ATTTGGTATC TGCGCTCTGC TGAAGCCAGT      2640

TACCTTCGGA AAAAGAGTTG GTAGCTCTTG ATCCGGCAAA CAAACCACCG CTGGTAGCGG      2700

TGGTTTTTTT GTTTGCAAGC AGCAGATTAC GCGCAGAAAA AAAGGATCTC AAGAAGATCC      2760

TTTGATCTTT TCTACGGGGT CTGACGCTCA GTGGAACGAA AACTCACGTT AAGGGATTTT      2820

GGTCATGAGA TTATCAAAAA GGATCTTCAC CTAGATCCTT TTAAATTAAA AATGAAGTTT      2880

TAAATCAATC TAAAGTATAT ATGAGTAAAC TTGGTCTGAC AGTTACCAAT GCTTAATCAG      2940

TGAGGCACCT ATCTCAGCGA TCTGTCTATT TCGTTCATCC ATAGTTGCCT GACTCCCCGT      3000

CGTGTAGATA ACTACGATAC GGGAGGGCTT ACCATCTGGC CCCAGTGCTG CAATGATACC      3060

GCGAGACCCA CGCTCACCGG CTCCAGATTT ATCAGCAATA AACCAGCCAG CCGGAAGGGC      3120

CGAGCGCAGA AGTGGTCCTG CAACTTTATC CGCCTCCATC CAGTCTATTA ATTGTTGCCG      3180

GGAAGCTAGA GTAAGTAGTT CGCCAGTTAA TAGTTTGCGC AACGTTGTTG CCATTGCTAC      3240

AGGCATCGTG GTGTCACGCT CGTCGTTTGG TATGGCTTCA TTCAGCTCCG GTTCCCAACG      3300

ATCAAGGCGA GTTACATGAT CCCCCATGTT GTGCAAAAAA GCGGTTAGCT CCTTCGGTCC      3360

TCCGATCGTT GTCAGAAGTA AGTTGGCCGC AGTGTTATCA CTCATGGTTA TGGCAGCACT      3420
```

-continued

```
GCATAATTCT CTTACTGTCA TGCCATCCGT AAGATGCTTT TCTGTGACTG GTGAGTACTC    3480

AACCAAGTCA TTCTGAGAAT AGTGTATGCG GCGACCGAGT TGCTCTTGCC CGGCGTCAAC    3540

ACGGGATAAT ACCGCGCCAC ATAGCAGAAC TTTAAAAGTG CTCATCATTG GAAAACGTTC    3600

TTCGGGGCGA AAACTCTCAA GGATCTTACC GCTGTTGAGA TCCAGTTCGA TGTAACCCAC    3660

TCGTGCACCC AACTGATCTT CAGCATCTTT TACTTTCACC AGCGTTTCTG GGTGAGCAAA    3720

AACAGGAAGG CAAAATGCCG CAAAAAGGG AATAAGGGCG ACACGGAAAT GTTGAATACT     3780

CATACTCTTC CTTTTTCAAT ATTATTGAAG CATTTATCAG GGTTATTGTC TCATGAGCGG    3840

ATACATATTT GAATGTATTT AGAAAAATAA ACAAAAAGAG TTTGTAGAAA CGCAAAAAGG    3900

CCATCCGTCA GGATGGCCTT CTGCTTAATT TGATGCCTGG CAGTTTATGG CGGGCGTCCT    3960

GCCCGCCACC CTCCGGGCCG TTGCTTCGCA ACGTTCAAAT CCGCTCCCGG CGGATTTGTC    4020

CTACTCAGGA GAGCGTTCAC CGACAAACAA CAGATAAAAC GAAAGGCCCA GTCTTTCGAC    4080

TGAGCCTTTC GTTTTATTTG ATGCCTGGCA GTTCCCTACT CTCGCATGGG GAGACCCCAC    4140

ACTACCATCG GCGCTACGGC GTTTCACTTC TGAGTTCGGC ATGGGGTCAG GTGGGACCAC    4200

CGCGCTACTG CCGCCAGGCA AACTGTTTTA TCAGACCGCT TCTGCGTTCT GATTTAATCT    4260

GTATCAGGCT GAAAATCTTC TCTCATCCGC CAAAACAGCC AAGCTTGGCT GCAGCCATGG    4320

TCTGTTTCCT GTGTGAAATT GTTATCCGCT CACAATTCCA CACATTATAC GAGCCGGATG    4380

ATTAATTGTC AACAGCTCAT TTCAGAATAT TTGCCAGAAC CGTTTATATG TCGGCGCAAA    4440

AAACATTATC CAGAACGGGA GTGCGCCTTG AGCGACACGA ATTATGCAGT GATTTACGAC    4500

CTGCACAGCC AATCCACAGC TTCCGATGGC TGCCTGACGC CAGAAGCATT GGTGCACCGT    4560

GCAGTCGATG ATAAGCTGTC AAACATGAGA ATT                                 4593
```

(2) INFORMATION FOR SEQ ID NO:2:

(i) SEQUENCE CHARACTERISTICS:
        (A) LENGTH: 4476 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Vector pSE380

(xi) SEQUENCE DESCRIPTION: SEQ ID NO:2:

```
AATTCTCATG TTTGACAGCT TATCATCGAC TGCACGGTGC ACCAATGCTT CTGGCGTCAG     60

GCAGCCATCG GAAGCTGTGG TATGGCTGTG CAGGTCGTAA ATCACTGCAT AATTCGTGTC    120

GCTCAAGGCG CACTCCCGTT CTGGATAATG TTTTTTGCGC CGACATCATA ACGGTTCTGG    180

CAAATATTCT GAAATGAGCT GTTGACAATT AATCATCCGG CTCGTATAAT GTGTGGAATT    240

GTGAGCGGAT AACAATTTCA CACAGGAAAC AGACCATGGC TGGTGACCAC GTCGTGGAAT    300

GCCTTCGAAT TCAGCACCTG CACATGGGAC GTCGACCTGA GGTAATTATA CCCGGGCCC     360

TATATATGGA TCCAATTGCA ATGATCATCA TGACAGATCT GCGCGCGATC GATATCAGCG    420

CTTTAAATTT GCGCATGCTA GCTATAGTTC TAGAGGTACC GGTTGTTAAC GTTAGCCGGC    480

TACGTATACT CCGGAATATT AATAGGCCTA GGATGCATAT GGCGGCCGCC TGCAGCTGGC    540

GCCATCGATA CGCGTACGTC GCGACCGCGG ACATGTACAG AGCTCGAGAA GTACTAGTGG    600
```

```
CCACGTGGGC CGTGCACCTT AAGCTTGGCT GTTTTGGCGG ATGAGAGAAG ATTTTCAGCC    660

TGATACAGAT TAAATCAGAA CGCAGAAGCG GTCTGATAAA ACAGAATTTG CCTGGCGGCA    720

GTAGCGCGGT GGTCCCACCT GACCCCATGC CGAACTCAGA AGTGAAACGC CGTAGCGCCG    780

ATGGTAGTGT GGGGTCTCCC CATGCGAGAG TAGGGAACTG CCAGGCATCA AATAAAACGA    840

AAGGCTCAGT CGAAAGACTG GGCCTTTCGT TTTATCTGTT GTTTGTCGGT GAACGCTCTC    900

CTGAGTAGGA CAAATCCGCC GGGAGCGGAT TTGAACGTTG CGAAGCAACG GCCCGGAGGG    960

TGGCGGGCAG GACGCCCGCC ATAAACTGCC AGGCATCAAA TTAAGCAGAA GGCCATCCTG   1020

ACGGATGGCC TTTTTGCGTT TCTACAAACT CTTTTTGTTT ATTTTTCTAA ATACATTCAA   1080

ATATGTATCC GCTCATGAGA CAATAACCCT GATAAATGCT TCAATAATAT TGAAAAAGGA   1140

AGAGTATGAG TATTCAACAT TTCCGTGTCG CCCTTATTCC CTTTTTTGCG GCATTTTGCC   1200

TTCCTGTTTT TGCTCACCCA GAAACGCTGG TGAAAGTAAA AGATGCTGAA GATCAGTTGG   1260

GTGCACGAGT GGGTTACATC GAACTGGATC TCAACAGCGG TAAGATCCTT GAGAGTTTTC   1320

GCCCCGAAGA ACGTTTTCCA ATGATGAGCA CTTTTAAAGT TCTGCTATGT GGCGCGGTAT   1380

TATCCCGTGT TGACGCCGGG CAAGAGCAAC TCGGTCGCCG CATACACTAT TCTCAGAATG   1440

ACTTGGTTGA GTACTCACCA GTCACAGAAA AGCATCTTAC GGATGGCATG ACAGTAAGAG   1500

AATTATGCAG TGCTGCCATA ACCATGAGTG ATAACACTGC GGCCAACTTA CTTCTGACAA   1560

CGATCGGAGG ACCGAAGGAG CTAACCGCTT TTTTGCACAA CATGGGGGAT CATGTAACTC   1620

GCCTTGATCG TTGGGAACCG GAGCTGAATG AAGCCATACC AAACGACGAG CGTGACACCA   1680

CGATGCCTGT AGCAATGGCA ACAACGTTGC GCAAACTATT AACTGGCGAA CTACTTACTC   1740

TAGCTTCCCG GCAACAATTA ATAGACTGGA TGGAGGCGGA TAAAGTTGCA GGACCACTTC   1800

TGCGCTCGGC CCTTCCGGCT GGCTGGTTTA TTGCTGATAA ATCTGGAGCC GGTGAGCGTG   1860

GGTCTCGCGG TATCATTGCA GCACTGGGGC CAGATGGTAA GCCCTCCCGT ATCGTAGTTA   1920

TCTACACGAC GGGGAGTCAG GCAACTATGG ATGAACGAAA TAGACAGATC GCTGAGATAG   1980

GTGCCTCACT GATTAAGCAT TGGTAACTGT CAGACCAAGT TTACTCATAT ATACTTTAGA   2040

TTGATTTAAA ACTTCATTTT TAATTTAAAA GGATCTAGGT GAAGATCCTT TTTGATAATC   2100

TCATGACCAA AATCCCTTAA CGTGAGTTTT CGTTCCACTG AGCGTCAGAC CCCGTAGAAA   2160

AGATCAAAGG ATCTTCTTGA GATCCTTTTT TTCTGCGCGT AATCTGCTGC TTGCAAACAA   2220

AAAAACCACC GCTACCAGCG GTGGTTTGTT TGCCGGATCA AGAGCTACCA ACTCTTTTTC   2280

CGAAGGTAAC TGGCTTCAGC AGAGCGCAGA TACCAAATAC TGTCCTTCTA GTGTAGCCGT   2340

AGTTAGGCCA CCACTTCAAG AACTCTGTAG CACCGCCTAC ATACCTCGCT CTGCTAATCC   2400

TGTTACCAGT GGCTGCTGCC AGTGGCGATA AGTCGTGTCT TACCGGGTTG GACTCAAGAC   2460

GATAGTTACC GGATAAGGCG CAGCGGTCGG GCTGAACGGG GGGTTCGTGC ACACAGCCCA   2520

GCTTGGAGCG AACGACCTAC ACCGAACTGA GATACCTACA GCGTGAGCTA TGAGAAAGCG   2580

CCACGCTTCC CGAAGGGAGA AAGGCGGACA GGTATCCGGT AAGCGGCAGG GTCGGAACAG   2640

GAGAGCGCAC GAGGGAGCTT CCAGGGGGAA ACGCCTGGTA TCTTTATAGT CCTGTCGGGT   2700

TTCGCCACCT CTGACTTGAG CGTCGATTTT TGTGATGCTC GTCAGGGGGG CGGAGCCTAT   2760

GGAAAAACGC CAGCAACGCG GCCTTTTTAC GGTTCCTGGC CTTTTGCTGG CCTTTTGCTC   2820

ACATGTTCTT TCCTGCGTTA TCCCCTGATT CTGTGGATAA CCGTATTACC GCCTTTGAGT   2880

GAGCTGATAC CGCTCGCCGC AGCCGAACGA CCGAGCGCAG CGAGTCAGTG AGCGAGGAAG   2940
```

```
CGGAAGAGCG CCTGATGCGG TATTTTCTCC TTACGCATCT GTGCGGTATT TCACACCGCA      3000

TATGGTGCAC TCTCAGTACA ATCTGCTCTG ATGCCGCATA GTTAAGCCAG TATACACTCC      3060

GCTATCGCTA CGTGACTGGG TCATGGCTGC GCCCCGACAC CCGCCAACAC CCGCTGACGC      3120

GCCCTGACGG GCTTGTCTGC TCCCGGCATC CGCTTACAGA CAAGCTGTGA CCGTCTCCGG      3180

GAGCTGCATG TGTCAGAGGT TTTCACCGTC ATCACCGAAA CGCGCGAGGC AGCAGATCAA      3240

TTCGCGCGCG AAGGCGAAGC GGCATGCATT TACGTTGACA CCATCGAATG GCGCAAAACC      3300

TTTCGCGGTA TGGCATGATA GCGCCCGGAA GAGAGTCAAT TCAGGGTGGT GAATGTGAAA      3360

CCAGTAACGT TATACGATGT CGCAGAGTAT GCCGGTGTCT CTTATCAGAC CGTTTCCCGC      3420

GTGGTGAACC AGGCCAGCCA CGTTTCTGCG AAAACGCGGG AAAAAGTGGA AGCGGCGATG      3480

GCGGAGCTGA ATTACATTCC CAACCGCGTG GCACAACAAC TGGCGGGCAA ACAGTCGTTG      3540

CTGATTGGCG TTGCCACCTC CAGTCTGGCC CTGCACGCGC CGTCGCAAAT TGTCGCGGCG      3600

ATTAAATCTC GCGCCGATCA ACTGGGTGCC AGCGTGGTGG TGTCGATGGT AGAACGAAGC      3660

GGCGTCGAAG CCTGTAAAGC GGCGGTGCAC AATCTTCTCG CGCAACGCGT CAGTGGGCTG      3720

ATCATTAACT ATCCGCTGGA TGACCAGGAT GCCATTGCTG TGGAAGCTGC CTGCACTAAT      3780

GTTCCGGCGT TATTTCTTGA TGTCTCTGAC CAGACACCCA TCAACAGTAT TATTTTCTCC      3840

CATGAAGACG GTACGCGACT GGGCGTGGAG CATCTGGTCG CATTGGGTCA CCAGCAAATC      3900

GCGCTGTTAG CGGGCCCATT AAGTTCTGTC TCGGCGCGTC TGCGTCTGGC TGGCTGGCAT      3960

AAATATCTCA CTCGCAATCA AATTCAGCCG ATAGCGGAAC GGGAAGGCGA CTGGAGTGCC      4020

ATGTCCGGTT TTCAACAAAC CATGCAAATG CTGAATGAGG GCATCGTTCC CACTGCGATG      4080

CTGGTTGCCA ACGATCAGAT GGCGCTGGGC GCAATGCGCG CCATTACCGA GTCCGGGCTG      4140

CGCGTTGGTG CGGATATCTC GGTAGTGGGA TACGACGATA CCGAAGACAG CTCATGTTAT      4200

ATCCCGCCGT TAACCACCAT CAAACAGGAT TTTCGCCTGC TGGGGCAAAC CAGCGTGGAC      4260

CGCTTGCTGC AACTCTCTCA GGGCCAGGCG GTGAAGGGCA ATCAGCTGTT GCCCGTCTCA      4320

CTGGTGAAAA GAAAACCAC CCTGGCGCCC AATACGCAAA CCGCCTCTCC CCGCGCGTTG      4380

GCCGATTCAT TAATGCAGCT GGCACGACAG GTTTCCCGAC TGGAAAGCGG GCAGTGAGCG      4440

CAACGCAATT AATGTGAGTT AGCGCGAATT GATCTT                                4476

(2) INFORMATION FOR SEQ ID NO:3:

(i) SEQUENCE CHARACTERISTICS:
        (A) LENGTH: 1337 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Rat lens aldose reductase gene (xi) SEQUENCE DESCRIPTION: SEQ ID NO:3:

CTCTTGCGGG TCGTTGTGCG TAACTTGCAG CAATCATGGC TAGCCATCTG GAACTCAACA        60

ACGGCACCAA GATGCCCACC CTGGGTCTGG GCACCTGGAA GTCTCCTCCT GGCCAGGTGA       120

CCGAGGCTGT GAAGGTTGCT ATCGACATGG GGTATCGCCA CATTGACTGC GCCCAGGTGT       180

ACCAGAATGA GAAGGAGGTG GGGGTGGCCC TCCAGGAGAA GCTCAAGGAG CAGGTGGTGA       240
```

-continued

```
AGCGCCAGGA TCTCTTCATT GTCAGCAAGC TGTGGTGCAC GTTCCACGAC CAGAGCATGG      300

TGAAAGGGGC CTGCCAGAAG ACGCTGAGCG ACCTGCAGCT GGACTACCTG GACCTCTACC      360

TTATTCACTG GCCAACTGGC TTCAAGCCTG GGCCTGACTA TTTCCCCCTG GATGCATCGG      420

GAAACGTGAT TCCTAGTGAC ACCGATTTTG TGGACACTTG GACGGCTATG GAGCAACTAG      480

TGGATGAAGG TTTGGTAAAA GCAATCGGAG TCTCCAACTT CAACCCTCTT CAGATTGAGA      540

GGATCTTGAA CAAACCTGGC TTAAAGTATA AGCCTGCTGT TAACCAGATC GAGTGCCACC      600

CATACCTAAC TCAGGAGAAG CTGATTGAGT ACTGCCATTG CAAAGGCATC GTGGTGACTG      660

CATACAGTCC CCTTGGTTCT CCTGACAGGC CCTGGGCCAA GCCTGAGGAC CCCTCTCTCC      720

TGGAGGATCC CAGGATCAAG GAAATTGCAG CCAAGTACAA TAAAACTACA GCCCAGGTGC      780

TGATCCGGTT CCCCATCCAA AGGAACCTGG TCGTGATCCC CAAGTCTGTG ACACCAGCAC      840

GTATTGCTGA GAACTTTAAG GTCTTTGACT TTGAGCTGAG CAATGAGGAC ATGGCCACTC      900

TACTCAGCTA CAACAGGAAC TGGAGGGTGT GCGCCTTGAT GAGCTGTGCC AAACACAAGG      960

ATTACCCCTT CCACGCAGAA GTCTGAAGCT GTGGTGGACA ATCCTGCTC CTCCCCAAGC      1020

GACTTAACAC ATGTTCTTTC TGCCTCATCT GCCCTTGCAA GTGTCCCTCT GCACTGGGTG     1080

GCACCTTGCA GACCAGATGG TGAGAGTTTG TTAGTTTGAC GTAGAATGTG GAGGGCAGTA     1140

CCAGTAGCTG AGGAGTTTCT TCGGCCTTTC TTGGTCTTCT TCCCACCTGG AGGACTTTAA     1200

CACGAGTACC TTTTCCAACC AAAGAGAAAG CAAGATTTAT AGCCCAAGTC ATGCCACTAA     1260

CACTTAAATT TGAGTGCTTA GAACTCCAGT CCTATGGGGG TCAGACTTTT TGCCTCAAAT     1320

AAAAACTGCT TTTGTCG                                                    1337
```

(2) INFORMATION FOR SEQ ID NO:4:

(i) SEQUENCE CHARACTERISTICS:
        (A) LENGTH: 316 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Rat lens aldose reductase (xi) SEQUENCE DESCRIPTION: SEQ ID NO:4:

```
Met Ala Ser His Leu Glu Leu Asn Asn Gly Thr Lys Met Pro Thr Leu
 1               5                  10                  15

Gly Leu Gly Thr Trp Lys Ser Pro Gly Gln Val Thr Glu Ala Val
            20                  25                  30

Lys Val Ala Ile Asp Met Gly Tyr Arg His Ile Asp Cys Ala Gln Val
        35                  40                  45

Tyr Gln Asn Glu Lys Glu Val Gly Val Ala Leu Gln Glu Lys Leu Lys
    50                  55                  60

Glu Gln Val Val Lys Arg Gln Asp Leu Phe Ile Val Ser Lys Leu Trp
65                  70                  75                  80

Cys Thr Phe His Asp Gln Ser Met Val Lys Gly Ala Cys Gln Lys Thr
                85                  90                  95

Leu Ser Asp Leu Gln Leu Asp Tyr Leu Asp Leu Tyr Leu Ile His Trp
            100                 105                 110
```

```
Pro Thr Gly Phe Lys Pro Gly Pro Asp Tyr Phe Pro Leu Asp Ala Ser
        115                 120                 125

Gly Asn Val Ile Pro Ser Asp Thr Asp Phe Val Asp Thr Trp Thr Ala
130                 135                 140

Met Glu Gln Leu Val Asp Glu Gly Leu Val Lys Ala Ile Gly Val Ser
145                 150                 155                 160

Asn Phe Asn Pro Leu Gln Ile Glu Arg Ile Leu Asn Lys Pro Gly Leu
                165                 170                 175

Lys Tyr Lys Pro Ala Val Asn Gln Ile Glu Cys His Pro Tyr Leu Thr
            180                 185                 190

Gln Glu Lys Leu Ile Glu Tyr Cys His Cys Lys Gly Ile Val Val Thr
        195                 200                 205

Ala Tyr Ser Pro Leu Gly Ser Pro Asp Arg Pro Trp Ala Lys Pro Glu
    210                 215                 220

Asp Pro Ser Leu Leu Glu Asp Pro Arg Ile Lys Glu Ile Ala Ala Lys
225                 230                 235                 240

Tyr Asn Lys Thr Thr Ala Gln Val Leu Ile Arg Phe Pro Ile Gln Arg
                245                 250                 255

Asn Leu Val Val Ile Pro Lys Ser Val Thr Pro Ala Arg Ile Ala Glu
            260                 265                 270

Asn Phe Lys Val Phe Asp Phe Glu Leu Ser Asn Glu Asp Met Ala Thr
        275                 280                 285

Leu Leu Ser Tyr Asn Arg Asn Trp Arg Val Cys Ala Leu Met Ser Cys
    290                 295                 300

Ala Lys His Lys Asp Tyr Pro Phe His Ala Glu Val
305                 310                 315
```

(2) INFORMATION FOR SEQ ID NO:5:

(i) SEQUENCE CHARACTERISTICS:
        (A) LENGTH: 5181 base pairs
        (B) TYPE: nucleic acid
        (C) STRANDEDNESS: single
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Yeast shuttle vector YEp352

(xi) SEQUENCE DESCRIPTION: SEQ ID NO:5:

```
ATGACCATGA TTACGAATTC GAGCTCGGTA CCCGGGGATC CTCTAGAGTC GACCTGCAGG      60

CATGCAAGCT TGGCACTGGC CGTCGTTTTA CAACGTCGTG ACTGGGAAAA CCCTGGCGTT     120

ACCCAACTTA ATCGCCTTGC AGCACATCCC CCCTTCGCCA GCTGGCGTAA TAGCGAAGAG     180

GCCCGCACCG ATCGCCCTTC CCAACAGTTG CGCAGCCTGA ATGGCGAATG GCGCCTGATG     240

CGGTATTTTC TCCTTACGCA TCTGTGCGGT ATTTCACACC GCATAGGGTA ATAACTGATA     300

TAATTAAATT GAAGCTCTAA TTTGTGAGTT TAGTATACAT GCATTTACTT ATAATACAGT     360

TTTTTAGTTT TGCTGGCCGC ATCTTCTCAA ATATGCTTCC CAGCCTGCTT TTCTGTAACG     420

TTCACCCTCT ACCTTAGCAT CCCTTCCCTT TGCAAATAGT CCTCTTCCAA CAATAATAAT     480

GTCAGATCCT GTAGAGACCA CATCATCCAC GGTTCTATAC TGTTGACCCA ATGCGTCTCC     540

CTTGTCATCT AAACCCACAC CGGGTGTCAT AATCAACCAA TCGTAACCTT CATCTCTTCC     600
```

| | |
|---|---|
| ACCCATGTCT CTTTGAGCAA TAAAGCCGAT AACAAAATCT TTGTCGCTCT TCGCAATGTC | 660 |
| AACAGTACCC TTAGTATATT CTCCAGTAGA TAGGGAGCCC TTGCATGACA ATTCTGCTAA | 720 |
| CATCAAAAGG CCTCTAGGTT CCTTTGTTAC TTCTTCTGCC GCCTGCTTCA AACCGCTAAC | 780 |
| AATACCTGGG CCCACCACAC CGTGTGCATT CGTAATGTCT GCCCATTCTG CTATTCTGTA | 840 |
| TACACCCGCA GAGTACTGCA ATTTGACTGT ATTACCAATG TCAGCAAATT TTCTGTCTTC | 900 |
| GAAGAGTAAA AAATTGTACT TGGCGGATAA TGCCTTTAGC GGCTTAACTG TGCCCTCCAT | 960 |
| GGAAAAATCA GTCAAGATAT CCACATGTGT TTTTAGTAAA CAAATTTTGG GACCTAATGC | 1020 |
| TTCAACTAAC TCCAGTAATT CCTTGGTGGT ACGAACATCC AATGAAGCAC ACAAGTTTGT | 1080 |
| TTGCTTTTCG TGCATGATAT TAAATAGCTT GGCAGCAACA GGACTAGGAT GAGTAGCAGC | 1140 |
| ACGTTCCTTA TATGTAGCTT TCGACATGAT TTATCTTCGT TTCGGTTTTT GTTCTGTGCA | 1200 |
| GTTGGGTTAA GAATACTGGG CAATTTCATG TTTCTTCAAC ACTACATATG CGTATATATA | 1260 |
| CCAATCTAAG TCTGTGCTCC TTCCTTCGTT CTTCCTTCTG TTCGGAGATT ACCGAATCAA | 1320 |
| AAAAATTTCA AAGAAACCGA ATCAAAAAA AGAATAAAA AAAAAATGAT GAATTGAAAA | 1380 |
| GCTCTTGTTA CCCATCATTG AATTTTGAAC ATCCGAACCT GGGAGTTTTC CCTGAAACAG | 1440 |
| ATAGTATATT TGAACCTGTA TAATAATATA TAGTCTAGCG CTTTACGGAA GACAATGTAT | 1500 |
| GTATTTCGGT TCCTGGAGAA ACTATTGCAT CTATTGCATA GGTAATCTTG CACGTCGCAT | 1560 |
| CCCCGGTTCA TTTTCTGCGT TTCCATCTTG CACTTCAATA GCATATCTTT GTTAACGAAG | 1620 |
| CATCTGTGCT TCATTTTGTA GAACAAAAAT GCAACGCGAG AGCGCTAATT TTTCAAACAA | 1680 |
| AGAATCTGAG CTGCATTTTT ACAGAACAGA AATGCAACGC GAAAGCGCTA TTTTACCAAC | 1740 |
| GAAGAATCTG TGCTTCATTT TTGTAAAACA AAAATGCAAC GCGAGAGCGC TAATTTTTCA | 1800 |
| AACAAAGAAT CTGAGCTGCA TTTTTACAGA ACAGAAATGC AACGCGAGAG CGCTATTTTA | 1860 |
| CCAACAAAGA ATCTATACTT CTTTTTTGTT CTACAAAAAT GCATCCCGAG AGCGCTATTT | 1920 |
| TTCTAACAAA GCATCTTAGA TTACTTTTTT TCTCCTTTGT GCGCTCTATA ATGCAGTCTC | 1980 |
| TTGATAACTT TTTGCACTGT AGGTCCGTTA AGGTTAGAAG AAGGCTACTT TGGTGTCTAT | 2040 |
| TTTCTCTTCC ATAAAAAAAG CCTGACTCCA CTTCCCGCGT TTACTGATTA CTAGCGAAGC | 2100 |
| TGCGGGTGCA TTTTTTCAAG ATAAAGGCAT CCCCGATTAT ATTCTATACC GATGTGGATT | 2160 |
| GCGCATACTT TGTGAACAGA AAGTGATAGC GTTGATGATT CTTCATTGGT CAGAAAATTA | 2220 |
| TGAACGGTTT CTTCTATTTT GTCTCTATAT ACTACGTATA GGAAATGTTT ACATTTTCGT | 2280 |
| ATTGTTTTCG ATTCACTCTA TGAATAGTTC TTACTACAAT TTTTTTGTCT AAAGAGTAAT | 2340 |
| ACTAGAGATA AACATAAAAA ATGTAGAGGT CGAGTTTAGA TGCAAGTTCA AGGAGCGAAA | 2400 |
| GGTGGATGGG TAGGTTATAT AGGGATATAG CACAGAGATA TATAGCAAAG AGATACTTTT | 2460 |
| GAGCAATGTT TGTGGAAGCG GTATTCGCAA TATTTTAGTA GCTCGTTACA GTCCGGTGCG | 2520 |
| TTTTTGGTTT TTTGAAAGTG CGTCTTCAGA GCGCTTTTGG TTTTCAAAAG CGCTCTGAAG | 2580 |
| TTCCTATACT TTCTAGCTAG AGAATAGGAA CTTCGGAATA GGAACTTCAA AGCGTTTCCG | 2640 |
| AAAACGAGCG CTTCCGAAAA TGCAACGCGA GCTGCGCACA TACAGCTCAC TGTTCACGTC | 2700 |
| GCACCTATAT CTGCGTGTTG CCTGTATATA TATATACATG AGAAGAACGG CATAGTGCGT | 2760 |
| GTTTATGCTT AAATGCGTTA TGGTGCACTC TCAGTACAAT CTGCTCTGAT GCCGCATAGT | 2820 |
| TAAGCCAGCC CCGACACCCG CCAACACCCG CTGACGCGCC CTGACGGGCT TGTCTGCTCC | 2880 |
| CGGCATCCGC TTACAGACAA GCTGTGACCG TCTCCGGGAG CTGCATGTGT CAGAGGTTTT | 2940 |

-continued

```
CACCGTCATC ACCGAAACGC GCGAGACGAA AGGGCCTCGT GATACGCCTA TTTTTATAGG      3000

TTAATGTCAT GATAATAATG GTTTCTTAGA CGTCAGGTGG CACTTTTCGG GGAAATGTGC      3060

GCGGAACCCC TATTTGTTTA TTTTTCTAAA TACATTCAAA TATGTATCCG CTCATGAGAC      3120

AATAACCCTG ATAAATGCTT CAATAATATT GAAAAAGGAA GAGTATGAGT ATTCAACATT      3180

TCCGTGTCGC CCTTATTCCC TTTTTTGCGG CATTTTGCCT TCCTGTTTTT GCTCACCCAG      3240

AAACGCTGGT GAAAGTAAAA GATGCTGAAG ATCAGTTGGG TGCACGAGTG GGTTACATCG      3300

AACTGGATCT CAACAGCGGT AAGATCCTTG AGAGTTTTCG CCCCGAAGAA CGTTTTCCAA      3360

TGATGAGCAC TTTTAAAGTT CTGCTATGTG GCGCGGTATT ATCCCGTATT GACGCCGGGC      3420

AAGAGCAACT CGGTCGCCGC ATACACTATT CTCAGAATGA CTTGGTTGAG TACTCACCAG      3480

TCACAGAAAA GCATCTTACG GATGGCATGA CAGTAAGAGA ATTATGCAGT GCTGCCATAA      3540

CCATGAGTGA TAACACTGCG GCCAACTTAC TTCTGACAAC GATCGGAGGA CCGAAGGAGC      3600

TAACCGCTTT TTTGCACAAC ATGGGGGATC ATGTAACTCG CCTTGATCGT TGGGAACCGG      3660

AGCTGAATGA AGCCATACCA AACGACGAGC GTGACACCAC GATGCCTGTA GCAATGGCAA      3720

CAACGTTGCG CAAACTATTA ACTGGCGAAC TACTTACTCT AGCTTCCCGG CAACAATTAA      3780

TAGACTGGAT GGAGGCGGAT AAAGTTGCAG GACCACTTCT GCGCTCGGCC CTTCCGGCTG      3840

GCTGGTTTAT TGCTGATAAA TCTGGAGCCG GTGAGCGTGG GTCTCGCGGT ATCATTGCAG      3900

CACTGGGGCC AGATGGTAAG CCCTCCCGTA TCGTAGTTAT CTACACGACG GGGAGTCAGG      3960

CAACTATGGA TGAACGAAAT AGACAGATCG CTGAGATAGG TGCCTCACTG ATTAAGCATT      4020

GGTAACTGTC AGACCAAGTT TACTCATATA TACTTTAGAT TGATTTAAAA CTTCATTTTT      4080

AATTTAAAAG GATCTAGGTG AAGATCCTTT TTGATAATCT CATGACCAAA ATCCCTTAAC      4140

GTGAGTTTTC GTTCCACTGA GCGTCAGACC CCGTAGAAAA GATCAAAGGA TCTTCTTGAG      4200

ATCCTTTTTT TCTGCGCGTA ATCTGCTGCT TGCAAACAAA AAAACCACCG CTACCAGCGG      4260

TGGTTTGTTT GCCGGATCAA GAGCTACCAA CTCTTTTTCC GAAGGTAACT GGCTTCAGCA      4320

GAGCGCAGAT ACCAAATACT GTCCTTCTAG TGTAGCCGTA GTTAGGCCAC CACTTCAAGA      4380

ACTCTGTAGC ACCGCCTACA TACCTCGCTC TGCTAATCCT GTTACCAGTG GCTGCTGCCA      4440

GTGGCGATAA GTCGTGTCTT ACCGGGTTGG ACTCAAGACG ATAGTTACCG GATAAGGCGC      4500

AGCGGTCGGG CTGAACGGGG GGTTCGTGCA CACAGCCCAG CTTGGAGCGA ACGACCTACA      4560

CCGAACTGAG ATACCTACAG CGTGAGCATT GAGAAAGCGC CACGCTTCCC GAAGGGAGAA      4620

AGGCGGACAG GTATCCGGTA AGCGGCAGGG TCGGAACAGG AGAGCGCACG AGGGAGCTTC      4680

CAGGGGGAAA CGCCTGGTAT CTTTATAGTC CTGTCGGGTT TCGCCACCTC TGACTTGAGC      4740

GTCGATTTTT GTGATGCTCG TCAGGGGGGC GGAGCCTATG GAAAAACGCC AGCAACGCGG      4800

CCTTTTTACG GTTCCTGGCC TTTTGCTGGC CTTTTGCTCA CATGTTCTTT CCTGCGTTAT      4860

CCCCTGATTC TGTGGATAAC CGTATTACCG CCTTTGAGTG AGCTGATACC GCTCGCCGCA      4920

GCCGAACGAC CGAGCGCAGC GAGTCAGTGA GCGAGGAAGC GGAAGAGCGC CCAATACGCA      4980

AACCGCCTCT CCCCGCGCGT TGGCCGATTC ATTAATCCAG CTGGCACGAC AGGTTTCCCG      5040

ACTGGAAAGC GGGCAGTGAG CGCAACGCAA TTAATGTGAG TTACCTCACT CATTAGGCAC      5100

CCCAGGCTTT ACACTTTATG CTTCCGGCTC GTATGTTGTG TGGAATTGTG AGCGGATAAC      5160

AATTTCACAC AGGAAACAGC T                                                5181
```

(2) INFORMATION FOR SEQ ID NO:6:

(i) SEQUENCE CHARACTERISTICS:
    (A) LENGTH: 506 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: E. coli methylglyoxal synthase gene (xi) SEQUENCE DESCRIPTION: SEQ ID NO:6:

```
TAAGTGCTTA CAGTAATCTG TAGGAAAGTT AACTACGGAT GTACATTATG GAACTGACGA    60

CTCGCACTTT ACCTGCGCGG AAACATATTG CGCTGGTGGC ACACGATCAC TGCAAACAAA   120

TGCTGATGAG CTGGGTGGAA CGGCATCAAC CGTTACTGGA ACAACACGTA CTGTATGCAA   180

CAGGCACTAC CGGTAACTTA ATTTCCCGCG CGACCGGCAT GAACGTCAAC GCGATGTTGA   240

GTGGCCCAAT GGGGGGTGAC CAGCAGGTTG GCGCATTGAT CTCAGAAGGG AAAATTGATG   300

TATTGATTTT CTTCTGGGAT CCACTAAATG CCGTGCCGCA CGATCCTGAC GTGAAAGCCT   360

TGCTGCGTCT GGCGACGGTA TGGAACATTC CGGTCGCCAC CAACGTGGCA ACGGCAGACT   420

TCATAATCCA GTCGCCGCAT TTCAACGACG CGGTCGATAT TCTGATCCCC GATTATCAGC   480

GTTATCTCGC GGACCGTCTG AAGTAA                                        506
```

(2) INFORMATION FOR SEQ ID NO:7:

(i) SEQUENCE CHARACTERISTICS:
    (A) LENGTH: 3524 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Pyridine nucleotide transhydrogenase gene (xi) SEQUENCE DESCRIPTION: SEQ ID NO:7:

```
CATAAAAATA ATCCTTCGCC TTGCGCAAAC CAGGTACTGG TATTGTTATT AACGAGAAAC    60

GTGGCTGATT ATTGCATTTA AACGGTGTAA CTGTCTGCGT CATTTTTCAT ATCACATTCC   120

TTAAGCCAAT TTTAATCCTG CTCAAATGAC CGTCTATGCT TAAAAAACAG CCGTATCAGC   180

ATCATTACTA CTGAAGCAAC TGAATTGTAT AAGTTAATTT AATGTAAGT AGTGATTCGT    240

GCCGGGGCGA TGTCTCGTTT TACCCGACCG TCGAAGACAA TTATCAGTCT TTATCCGGCG   300

TTCTAAGGTG TTTATCCCAC TATCACGGCT GAATCGTTAA TATTTTGCGA GTTCACGCCG   360

AAATACTGAT TTTTGGCGCT AGATCACAGG CATAATTTTC AGTACGTTAT AGGGCGTTTG   420

TTACTAATTT ATTTTAACGG AGTAACATTT AGCTCGTACA TGAGCAGCTT GTGTGGCTCC   480

TGACACAGGC AAACCATCAT CAATAAAACC GATGGAAGGG AATATCATGC GAATTGGCAT   540

ACCAAGAGAA CGGTTAACCA ATGAAACCCG TGTTGCAGCA ACGCCAAAAA CAGTGGAACA   600

GCTGCTGAAA CTGGGTTTTA CCGTCGCGGT AGAGAGCGGC GCGGGTCAAC TGGCAAGTTT   660

TGACGATAAA GCGTTTGTGC AAGCGGGCGC TGAAATTGTA GAAGGGAATA GCGTCTGGCA   720
```

-continued

```
GTCAGAGATC ATTCTGAAGG TCAATGCGCC GTTAGATGAT GAAATTGCGT TACTGAATCC      780

TGGGACAACG CTGGTGAGTT TTATCTGGCC TGCGCAGAAT CCGGAATTAA TGCAAAAACT      840

TGCGGAACGT AACGTGACCG TGATGGCGAT GGACTCTGTG CCGCGTATCT CACGCGCACA      900

ATCGCTGGAC GCACTAAGCT CGATGGCGAA CATCGCCGGT TATCGCGCCA TTGTTGAAGC      960

GGCACATGAA TTTGGGCGCT TCTTTACCGG GCAAATTACT GCGGCCGGGA AAGTGCCACC     1020

GGCAAAAGTG ATGGTGATTG GTGCGGGTGT TGCAGGTCTG GCCGCCATTG GCGCAGCAAA     1080

CAGTCTCGGC GCGATTGTGC GTGCATTCGA CACCCGCCCG GAAGTGAAAG AACAAGTTCA     1140

AAGTATGGGC GCGGAATTCC TCGAGCTGGA TTTTAAAGAG GAAGCTGGCA GCGGCGATGG     1200

CTATGCCAAA GTGATGTCGG ACGCGTTCAT CAAAGCGGAA ATGGAACTCT TTGCCGCCCA     1260

GGCAAAAGAG GTCGATATCA TTGTCACCAC CGCGCTTATT CCAGGCAAAC CAGCGCCGAA     1320

GCTAATTACC CGTGAAATGG TTGACTCCAT GAAGGCGGGC AGTGTGATTG TCGACCTGGC     1380

AGCCCAAAAC GGCGGCAACT GTGAATACAC CGTGCCGGGT GAAATCTTCA CTACGGAAAA     1440

TGGTGTCAAA GTGATTGGTT ATACCGATCT TCCGGGCCGT CTGCCGACGC AATCCTCACA     1500

GCTTTACGGC ACAAACCTCG TTAATCTGCT GAAACTGTTG TGCAAAGAGA AAGACGGCAA     1560

TATCACTGTT GATTTTGATG ATGTGGTGAT TCGCGGCGTG ACCGTGATCC GTGCGGGCGA     1620

AATTACCTGG CCGGCACCGC CGATTCAGGT ATCAGCTCAG CCGCAGGCGG CACAAAAAGC     1680

GGCACCGGAA GTGAAAACTG AGGAAAAATG TACCTGCTCA CCGTGGCGTA AATACGCGTT     1740

GATGGCGCTG GCAATCATTC TTTTTGGCTG GATGGCAAGC GTTGCGCCGA AGAATTCCT     1800

TGGGCACTTC ACCGTTTTCG CGCTGGCCTG CGTTGTCGGT TATTACGTGG TGTGGAATGT     1860

ATCGCACGCG CTGCATACAC CGTTGATGTC GGTCACCAAC GCGATTTCAG GGATTATTGT     1920

TGTCGGAGCA CTGTTGCAGA TTGGCCAGGG CGGCTGGGTT AGCTTCCTTA GTTTTATCGC     1980

GGTGCTTATA GCCAGCATTA ATATTTTCGG TGGCTTCACC GTGACTCAGC GCATGCTGAA     2040

AATGTTCCGC AAAAATTAAG GGGTAACATA TGTCTGGAGG ATTAGTTACA GCTGCATACA     2100

TTGTTGCCGC GATCCTGTTT ATCTTCAGTC TGGCCGGTCT TTCGAAACAT GAAACGTCTC     2160

GCCAGGGTAA CAACTTCGGT ATCGCCGGGA TGGCGATTGC GTTAATCGCA ACCATTTTTG     2220

GACCGGATAC GGGTAATGTT GGCTGGATCT TGCTGGCGAT GGTCATTGGT GGGGCAATTG     2280

GTATCCGTCT GGCGAAGAAA GTTGAAATGA CCGAAATGCC AGAACTGGTG GCGATCCTGC     2340

ATAGCTTCGT GGGTCTGGCG GCAGTGCTGG TTGGCTTTAA CAGCTATCTG CATCATGACG     2400

CGGGAATGGC ACCGATTCTG GTCAATATTC ACCTGACGGA AGTGTTCCTC GGTATCTTCA     2460

TCGGGGCGGT AACGTTCACG GGTTCGGTGG TGGCGTTCGG CAAACTGTGT GGCAAGATTT     2520

CGTCTAAACC ATTGATGCTG CCAAACCGTC ACAAAATGAA CCTGCGGCT CTGGTCGTTT      2580

CCTTCCTGCT GCTGATTGTA TTTGTTCGCA CGGACAGCGT CGGCCTGCAA GTGCTGGCAT     2640

TGCTGATAAT GACCGCAATT GCGCTGGTAT TCGGCTGGCA TTTAGTCGCC TCCATCGGTG     2700

GTGCAGATAT GCCAGTGGTG GTGTCGATGC TGAACTCGTA CTCCGGCTGG GCGGCTGCGG     2760

CTGCGGGCTT TATGCTCAGC AACGACCTGC TGATTGTGAC CGGTGCGCTG GTCGGTTCTT     2820

CGGGGGCTAT CCTTTCTTAC ATTATGTGTA AGGCGATGAA CCGTTCCTTT ATCAGCGTTA     2880

TTGCGGGTGG TTTCGGCACC GACGGCTCTT CTACTGGCGA TGATCAGGAA GTGGGTGAGC     2940

ACCGCGAAAT CACCGCAGAA GAGACAGCGG AACTGCTGAA AAACTCCCAT TCAGTGATCA     3000

TTACTCCGGG GTACGGCATG GCAGTCGCGC AGGCGCAATA TCCTGTCGCT GAAATTACTG     3060

AGAAATTGCG CGCTCGTGGT ATTAATGTGC GTTTCGGTAT CCACCCGGTC GCGGGGCGTT     3120
```

```
TGCCTGGACA TATGAACGTA TTGCTGGCTG AAGCAAAAGT ACCGTATGAC ATCGTGCTGG      3180

AAATGGACGA GATCAATGAT GACTTTGCTG ATACCGATAC CGTACTGGTG ATTGGTGCTA      3240

ACGATACGGT TAACCCGGCG GCGCAGGATG ATCCGAAGAG TCCGATTGCT GGTATGCCTG      3300

TGCTGGAAGT GTGGAAAGCG CAGAACGTGA TTGTCTTTAA ACGTTCGATG AACACTGGCT      3360

ATGCTGGTGT GCAAAACCCG CTGTTCTTCA AGGAAAACAC CCACATGCTG TTTGGTGACG      3420

CCAAAGCCAG CGTGGATGCA ATCCTGAAAG CTCTGTAACC CTCGACTCTG CTGAGGCCGT      3480

CACTCTTTAT TGAGATCGCT TAACAGAACG GCGATGCGAC TCTA                       3524
```

(2) INFORMATION FOR SEQ ID NO:8:

(i) SEQUENCE CHARACTERISTICS:
        (A) LENGTH: 510 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Pyridine nucleotide transhydrogenase, subunit A (xi) SEQUENCE DESCRIPTION: SEQ ID NO:8:

```
Met Arg Ile Gly Ile Pro Arg Glu Arg Leu Thr Asn Glu Thr Arg Val
1               5                   10                  15

Ala Ala Thr Pro Lys Thr Val Glu Gln Leu Leu Lys Leu Gly Phe Thr
            20                  25                  30

Val Ala Val Glu Ser Gly Ala Gly Gln Leu Ala Ser Phe Asp Asp Lys
        35                  40                  45

Ala Phe Val Gln Ala Gly Ala Glu Ile Val Glu Gly Asn Ser Val Trp
    50                  55                  60

Gln Ser Glu Ile Ile Leu Lys Val Asn Ala Pro Leu Asp Asp Glu Ile
65                  70                  75                  80

Ala Leu Leu Asn Pro Gly Thr Thr Leu Val Ser Phe Ile Trp Pro Ala
                85                  90                  95

Gln Asn Pro Glu Leu Met Gln Lys Leu Ala Glu Arg Asn Val Thr Val
            100                 105                 110

Met Ala Met Asp Ser Val Pro Arg Ile Ser Arg Ala Gln Ser Leu Asp
        115                 120                 125

Ala Leu Ser Ser Met Ala Asn Ile Ala Gly Tyr Arg Ala Ile Val Glu
    130                 135                 140

Ala Ala His Glu Phe Gly Arg Phe Phe Thr Gly Gln Ile Thr Ala Ala
145                 150                 155                 160

Gly Lys Val Pro Pro Ala Lys Val Met Val Ile Gly Ala Gly Val Ala
                165                 170                 175

Gly Leu Ala Ala Ile Gly Ala Ala Asn Ser Leu Gly Ala Ile Val Arg
            180                 185                 190

Ala Phe Asp Thr Arg Pro Glu Val Lys Glu Gln Val Gln Ser Met Gly
        195                 200                 205

Ala Glu Phe Leu Glu Leu Asp Phe Lys Glu Glu Ala Gly Ser Gly Asp
    210                 215                 220
```

-continued

```
Gly Tyr Ala Lys Val Met Ser Asp Ala Phe Ile Lys Ala Glu Met Glu
225                 230                 235                 240

Leu Phe Ala Ala Gln Ala Lys Glu Val Asp Ile Ile Val Thr Thr Ala
                245                 250                 255

Leu Ile Pro Gly Lys Pro Ala Pro Lys Leu Ile Thr Arg Glu Met Val
            260                 265                 270

Asp Ser Met Lys Ala Gly Ser Val Ile Val Asp Leu Ala Ala Gln Asn
        275                 280                 285

Gly Gly Asn Cys Glu Tyr Thr Val Pro Gly Glu Ile Phe Thr Thr Glu
    290                 295                 300

Asn Gly Val Lys Val Ile Gly Tyr Thr Asp Leu Pro Gly Arg Leu Pro
305                 310                 315                 320

Thr Gln Ser Ser Gln Leu Tyr Gly Thr Asn Leu Val Asn Leu Leu Lys
                325                 330                 335

Leu Leu Cys Lys Glu Lys Asp Gly Asn Ile Thr Val Asp Phe Asp Asp
            340                 345                 350

Val Val Ile Arg Gly Val Thr Val Ile Arg Ala Gly Glu Ile Thr Trp
        355                 360                 365

Pro Ala Pro Pro Ile Gln Val Ser Ala Gln Pro Gln Ala Ala Gln Lys
    370                 375                 380

Ala Ala Pro Glu Val Lys Thr Glu Glu Lys Cys Thr Cys Ser Pro Trp
385                 390                 395                 400

Arg Lys Tyr Ala Leu Met Ala Leu Ala Ile Ile Leu Phe Gly Trp Met
                405                 410                 415

Ala Ser Val Ala Pro Lys Glu Phe Leu Gly His Phe Thr Val Phe Ala
            420                 425                 430

Leu Ala Cys Val Val Gly Tyr Tyr Val Val Trp Asn Val Ser His Ala
        435                 440                 445

Leu His Thr Pro Leu Met Ser Val Thr Asn Ala Ile Ser Gly Ile Ile
    450                 455                 460

Val Val Gly Ala Leu Leu Gln Ile Gly Gln Gly Gly Trp Val Ser Phe
465                 470                 475                 480

Leu Ser Phe Ile Ala Val Leu Ile Ala Ser Ile Asn Ile Phe Gly Gly
                485                 490                 495

Phe Thr Val Thr Gln Arg Met Leu Lys Met Phe Arg Lys Asn
            500                 505                 510
```

(2) INFORMATION FOR SEQ ID NO:9:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:
        (A) ORGANISM: Pyridine nucleotide transhydrogenase, subunit B (xi) SEQUENCE DESCRIPTION: SEQ ID NO:9:

```
Met Ser Gly Gly Leu Val Thr Ala Ala Tyr Ile Val Ala Ala Ile Leu
1               5                   10                  15
```

```
Phe Ile Phe Ser Leu Ala Gly Leu Ser Lys His Glu Thr Ser Arg Gln
            20                  25                  30

Gly Asn Asn Phe Gly Ile Ala Gly Met Ala Ile Ala Leu Ile Ala Thr
                35                  40                  45

Ile Phe Gly Pro Asp Thr Gly Asn Val Gly Trp Ile Leu Leu Ala Met
            50                  55                  60

Val Ile Gly Gly Ala Ile Gly Ile Arg Leu Ala Lys Lys Val Glu Met
 65                  70                  75                  80

Thr Glu Met Pro Glu Leu Val Ala Ile Leu His Ser Phe Val Gly Leu
                    85                  90                  95

Ala Ala Val Leu Val Gly Phe Asn Ser Tyr Leu His His Asp Ala Gly
                100                 105                 110

Met Ala Pro Ile Leu Val Asn Ile His Leu Thr Glu Val Phe Leu Gly
            115                 120                 125

Ile Phe Ile Gly Ala Val Thr Phe Thr Gly Ser Val Val Ala Phe Gly
            130                 135                 140

Lys Leu Cys Gly Lys Ile Ser Ser Lys Pro Leu Met Leu Pro Asn Arg
145                 150                 155                 160

His Lys Met Asn Leu Ala Ala Leu Val Val Ser Phe Leu Leu Leu Ile
                165                 170                 175

Val Phe Val Arg Thr Asp Ser Val Gly Leu Gln Val Leu Ala Leu Leu
            180                 185                 190

Ile Met Thr Ala Ile Ala Leu Val Phe Gly Trp His Leu Val Ala Ser
            195                 200                 205

Ile Gly Gly Ala Asp Met Pro Val Val Ser Met Leu Asn Ser Tyr
            210                 215                 220

Ser Gly Trp Ala Ala Ala Ala Gly Phe Met Leu Ser Asn Asp Leu
225                 230                 235                 240

Leu Ile Val Thr Gly Ala Leu Val Gly Ser Ser Gly Ala Ile Leu Ser
                245                 250                 255

Tyr Ile Met Cys Lys Ala Met Asn Arg Ser Phe Ile Ser Val Ile Ala
            260                 265                 270

Gly Gly Phe Gly Thr Asp Gly Ser Ser Thr Gly Asp Asp Gln Glu Val
            275                 280                 285

Gly Glu His Arg Glu Ile Thr Ala Glu Glu Thr Ala Glu Leu Leu Lys
            290                 295                 300

Asn Ser His Ser Val Ile Ile Thr Pro Gly Tyr Gly Met Ala Val Ala
305                 310                 315                 320

Gln Ala Gln Tyr Pro Val Ala Glu Ile Thr Glu Lys Leu Arg Ala Arg
            325                 330                 335

Gly Ile Asn Val Arg Phe Gly Ile His Pro Val Ala Gly Arg Leu Pro
            340                 345                 350

Gly His Met Asn Val Leu Leu Ala Glu Ala Lys Val Pro Tyr Asp Ile
            355                 360                 365

Val Leu Glu Met Asp Glu Ile Asn Asp Asp Phe Ala Asp Thr Asp Thr
            370                 375                 380

Val Leu Val Ile Gly Ala Asn Asp Thr Val Asn Pro Ala Ala Gln Asp
385                 390                 395                 400

Asp Pro Lys Ser Pro Ile Ala Gly Met Pro Val Leu Glu Val Trp Lys
            405                 410                 415

Ala Gln Asn Val Ile Val Phe Lys Arg Ser Met Asn Thr Gly Tyr Ala
            420                 425                 430

Gly Val Gln Asn Pro Leu Phe Phe Lys Glu Asn Thr His Met Leu Phe
```

```
                    435              440              445
Gly Asp Ala Lys Ala Ser Val Asp Ala Ile Leu Lys Ala Leu
    450              455              460
```

(2) INFORMATION FOR SEQ ID NO:10:

(i) SEQUENCE CHARACTERISTICS:
        (A) LENGTH: 1139 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Glycerol dehydrogenase gene
        (B) STRAIN: E. coli (xi) SEQUENCE DESCRIPTION: SEQ ID NO:10:

```
TACGGCGTAA ACCGTGATGA GTAGAGATTT CCTCGTTAAT ACCTGGCGTA ATAAGTTAGT    60

GGCCCATTTA TGTAGGTCCC GCGACTACAC TAATTAGCAG ACCCGCTTAT GGACTTCGGC   120

GACTCTTGCG ACCAATCACC ACCCACTGTT TAAACAAAAT CCAAAACGAG TTAGGTGACA   180

GCTCTTTTCG AAATTTCTAC GACCAGACCA TCATCTTTAA CGCGGCAAAC CGCCACTTAC   240

AAGCGTTTTA CTCATGCTGG CAGACGCACC GTAGCGCCTC TGACGCGTCA CACCGCGTTA   300

AGAGCCATAG CCACCGCCTT TTTGGGAGCT ATGACGGTTT CGTGACCGTG TAAAGTACCC   360

ACAAGGCCAT CGCTAGCGTG GCTGATAGCG GAGATGGCTA CGTGGCACGT CGCGTAACAG   420

ACAATAGATG TGGCTACTCC CACTCAAACT GGCGATAGAC GACAACGGTT TATTGGGCTT   480

ATACCAGTAA CAGCTGTGGT TTTAGCAGCG ACCGCGTGGA CGTGCAGACA ATCGCCGCCC   540

ATAGCCGCTA CGCGACCGTT GGACCAAACT TCGCGCACGG ACGAGAGCAT CGCCGCGCTG   600

GTGGTACCGC CCGCCGTTCA CGTGGGTCCG ACGCGACCGT GACCGACTTG ACACGATGTT   660

GTGGGACGAC CTTCTTCCGC TTTTTCGCTA CGAACGACGG CTTGTCATGC ATCACTGAGG   720

CCGCGACCTC GCGCACTAAC TTCGCTTGTG GATAAACTCG CCACAACCAA AACTTTCACC   780

ACCAGACGAC GCCGCGTGCG TCACGTATTG CCGGACTGGC GATAGGGCCT GCGCGTAGTG   840

ATAATAGTGC CACTTTTTCA CCGTAAGCCA TGCGACTGCG TCGACCAAGA CCTTTTACGC   900

GGCCACCTCC TTTAGCTTTG GCATCGACGG GAATCGGTAC GCCATCCAAA CGTTATTGAG   960

AGCGAGTTGA CCTATAATTT CTTCTACAGG GCCCGTTTTA CGCTTAACAC CGTCTTCGCC  1020

GTACACGTCT TCCACTTTGG TAAGTGTTGT ACGGACCGCC GCGCTGCGGT CTAGTCCAAA  1080

TGCGGCGAGA CGACCATCGG CTGGTCATGC CAGTCGCAAA GGACGTTCTC ACCCTTATT   1139
```

(2) INFORMATION FOR SEQ ID NO:11:

(i) SEQUENCE CHARACTERISTICS:
        (A) LENGTH: 380 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO -continued (vi) ORIGINAL SOURCE:
  (A) ORGANISM: E. coli glycerol dehydrogenase (xi) SEQUENCE DESCRIPTION: SEQ ID NO:11:

```
Met Pro His Leu Ala Leu Leu Ile Ser Lys Gly Ala Ile Met Asp Arg
1               5                   10                  15

Ile Ile Gln Ser Pro Gly Lys Tyr Ile Gln Gly Ala Asp Val Ile Asn
            20                  25                  30

Arg Leu Gly Glu Tyr Leu Lys Pro Leu Xaa Glu Arg Trp Leu Val Val
        35                  40                  45

Gly Asp Lys Phe Val Leu Gly Phe Ala Gln Ser Thr Val Glu Lys Ser
    50                  55                  60

Phe Lys Asp Ala Gly Leu Val Val Glu Ile Ala Pro Phe Gly Gly Glu
65                  70                  75                  80

Cys Ser Gln Asn Glu Ile Asp Arg Leu Arg Gly Ile Ala Glu Thr Ala
                85                  90                  95

Gln Cys Gly Ala Ile Leu Gly Ile Gly Gly Gly Lys Thr Leu Asp Thr
                100                 105                 110

Ala Lys Ala Leu Ala His Phe Met Gly Val Pro Val Ala Ile Ala Pro
            115                 120                 125

Thr Ile Ala Ser Thr Asp Ala Pro Cys Ser Ala Leu Ser Val Ile Tyr
        130                 135                 140

Thr Asp Glu Gly Glu Phe Asp Arg Tyr Leu Leu Leu Pro Asn Asn Pro
145                 150                 155                 160

Asn Met Val Ile Val Asp Thr Lys Ile Val Ala Gly Ala Pro Ala Arg
                165                 170                 175

Leu Leu Ala Ala Gly Ile Gly Asp Ala Leu Ala Thr Trp Phe Glu Ala
                180                 185                 190

Arg Ala Cys Ser Arg Ser Gly Ala Thr Thr Met Ala Gly Gly Lys Cys
            195                 200                 205

Thr Gln Ala Ala Leu Ala Leu Ala Glu Leu Cys Tyr Asn Thr Leu Leu
        210                 215                 220

Glu Glu Gly Glu Lys Ala Met Leu Ala Ala Glu Gln His Val Val Thr
225                 230                 235                 240

Pro Ala Leu Glu Arg Val Ile Glu Ala Asn Thr Tyr Leu Ser Gly Val
                245                 250                 255

Gly Phe Glu Ser Gly Gly Leu Ala Ala Ala His Ala Val His Asn Gly
                260                 265                 270

Leu Thr Ala Ile Pro Asp Ala His His Tyr Tyr His Gly Glu Lys Val
        275                 280                 285

Ala Phe Gly Thr Leu Thr Gln Leu Val Leu Glu Asn Ala Pro Val Glu
    290                 295                 300

Glu Ile Glu Thr Val Ala Ala Leu Ser His Ala Val Gly Leu Pro Ile
305                 310                 315                 320

Thr Leu Ala Gln Leu Asp Ile Lys Glu Asp Val Pro Ala Lys Met Arg
            325                 330                 335

Ile Val Ala Glu Ala Ala Cys Ala Glu Gly Glu Thr Ile His Asn Met
                340                 345                 350

Pro Gly Gly Ala Thr Pro Asp Gln Val Tyr Ala Ala Leu Leu Val Ala
            355                 360                 365

Asp Gln Tyr Gly Gln Arg Phe Leu Gln Glu Trp Glu
370                 375                 380
```

BIBLIOGRAPHY

Ackerman, R. S., Cozzarelli, R., Epstein, W. (1974) *J. Bact.* 119:357–362.

Cameron, D. C. and C. L. Cooney (1986) *Bio/Technology* 4:651–654.

Ferguson, G. P., Chacko, A. D., Lee, C., Booth I. R. (1996) *J. Bact.* 178:3957–3961.

Franklin Associates, Ltd. (1994) "Life Cycle Assessment of Ethylene Glycol and Propylene Glycol Based Antifreeze," Franklin Associates, Prairie Village, Kans.

Freedberg, W. B., Kistler, W. S., Lin, E. C. C. (1971) *J. Bact.* 108:137–144.

Gait, A. J. "Propylene Oxide," In: E. G. Hancock (ed.), *Propylene and its Industrial Derivatives*, p. 273–297, John Wiley and Sons, New York, N.Y. (1973).

Ghalambor, M. A.; Heath, E. C. (1962) *J. Biol. Chem.* 237:2427–2433.

Hill, J. E., Myers, A. M., Koerner, T. J., Tzagoloff, A. (1986) *Yeast* 2:163–167.

Hopper, D. J., and Cooper, R. A. (1972) *Biochem J.* 128:321–329.

Kadner, R. J., Murphy, G. P., Stephens, C. M. (1992) *J. Gen. Microbio.* 138:2007–2014.

Kluyver and Schnellen (1937) *Enzymologia* 4:7–12.

Koob, M. D., Shaw, A. J., and Cameron, D. C. (1994) *Proc. N.Y. Acad. Sci.* 745:1–3.

Obradors, N., Badia, J., Baldoma, L., and Aguilar, J. (1988) *J. Bact.* 170:2159–2162.

Old, S. E., Sato, S., Kador, P. F., and Carper, D. A. (1990) *Proc. Natl. Acad. Sci.* 87:4942–4945.

Percy, D. S. and Harrison, D. H. T. (1996) Cloning, Expression and Characterization of Methylgyoxal Synthase from *Escherichia coli. American Society for Biochemistry and Molecular Biology Meeting Abstract, Protein Structure Section*, No. 1367, Jun. 2–6, 1996.

Sambrook, Fritsch, and Maniatis (1986) "Molecular Cloning, A Laboratory Manual," 2nd. Ed.

Sato, S., Old, S., Carper, D., and Kador, P. F. (1995) *Enzymology and Molecular Biology of Carbonyl Metabolism* 5, p. 259–268, H. Weiner et al. (Eds.), Plenum Press, New York.

Sawada, H.; Takagi, Y. (1964) *Biochim. Biophys. Acta,* 92:26–32.

Simon, E. S., Whitesides, G. M., Cameron, D. C., Weitz, D. J., and Cooney, C. L. (1987) *J. Org. Chem.* 52:4042–4044.

Sridhara, S.; Wu, T. T. (1969) *J. Biol. Chem.* 244:5233–5238.

Tran-Din, K. and G. Gottschalk (1985) *Arch. Microbiol.* 142:87–92.

What is claimed is:

1. A method of producing 1,2-propanediol by fermentation of sugars comprising: culturing a recombinant microorganism which expresses recombinant enzyme activity selected from the group consisting of recombinant aldose reductase activity, recombinant glycerol dehydrogenase activity, recombinant methylglyoxal synthase activity, recombinant pyridine nucleotide transferase activity, and combinations thereof in a medium containing a sugar carbon source other than a 6-deoxyhexose sugar, wherein the recombinant microorganism is cultured aerobically, whereby the sugar carbon source is metabolized by the recombinant microorganism into 1,2-propanediol.

2. The method of claim 1, wherein a recombinant *E. coli* is cultured.

3. The method of claim 1, wherein a recombinant microorganism transformed with a transformation vector containing a gene sequence selected from the group consisting of SEQ. ID. NO: 3, SEQ. ID. NO: 6, SEQ ID. NO: 7, SEQ. ID. NO: 10, and combinations thereof, is cultured.

4. The method of claim 1, wherein a recombinant microorganism transformed with a transformation vector containing a gene sequence selected from the group consisting of SEQ. ID. NO: 3, SEQ. ID. NO: 6, SEQ. ID. NO: 7, SEQ. ID. NO: 10, and combinations thereof, the gene sequence operationally linked to one or more promoter sequences whereby transcription of the gene sequence is controlled, is cultured.

5. The method of claim 4, wherein the promoter sequence is selected from the group consisting of lac, trc, tac, and phoA.

6. The method of claim 1, wherein a microorganism lacking enzyme activity selected from the group consisting of triose phosphate isomerase activity, glyoxalase I activity, and combinations thereof, is cultured.

7. The method of claim 6, wherein *E. coli* is cultured.

8. The method of claim 6, wherein *E. coli* strain AA200 is cultured.

9. The method of claim 1, wherein the recombinant microorganism is cultured in a medium containing a sugar carbon source selected from the group consisting of arabinose, fructose, galactose, glucose, lactose, maltose, sucrose, xylose, and combinations thereof.

10. The method of claim 1, further comprising the step of isolating the 1,2-propanediol formed.

\* \* \* \* \*